(12) United States Patent
Fagan et al.

(10) Patent No.: US 7,531,508 B2
(45) Date of Patent: May 12, 2009

(54) SPLICE VARIANT OF THE HUMAN PITUITARY GROWTH HORMONE

(75) Inventors: Richard Joseph Fagan, London (GB); Christopher Benjamin Phelps, London (GB); Tania Maria Rodrigues, London (GB); Melanie Yorke, Confignon (CH); Mariastella De Tiani, Geneva (CH)

(73) Assignee: Ares Trading S.A., Aubonne (CH)

( * ) Notice: Subject to any disclaimer, the term of this patent is extended or adjusted under 35 U.S.C. 154(b) by 418 days.

(21) Appl. No.: 10/537,142

(22) PCT Filed: Dec. 5, 2003

(86) PCT No.: PCT/GB03/05295

§ 371 (c)(1), (2), (4) Date: Nov. 10, 2005

(87) PCT Pub. No.: WO2004/050703

PCT Pub. Date: Jun. 17, 2004

(65) Prior Publication Data

US 2006/0275293 A1    Dec. 7, 2006

(30) Foreign Application Priority Data

Dec. 5, 2002    (GB) .............................. 0228441.2

(51) Int. Cl.
*A61K 38/27* (2006.01)
*C07K 14/475* (2006.01)

(52) U.S. Cl. ............................. 514/12; 514/2; 530/399
(58) Field of Classification Search ........................ None
See application file for complete search history.

(56) References Cited

U.S. PATENT DOCUMENTS 6,013,773 A * 1/2000 Kobayashi et al. .......... 530/399
6,914,046 B1 * 7/2005 Hirsch et al. .................. 514/12

OTHER PUBLICATIONS

Denoto, F.M. et al. "Human growth hormone DNA sequence and mRNA structure: possible alternative splicing" *Nucl. Acids Res.*, 1981, 9(15):3719-3730.
Lecomte, C.M. et al. "A new natural HGH variant-17.5 kd-produced by alternative splicing. An additional consensus sequence with might play a role in branchpoint selection" *Nucl. Acids Res.*, 1987, 15(16):6331-6348.
Masuda, N. et al. "Molecular cloning of cDNA encoding 20 kda variant human growth hormone and the alternative splicing mechanism" *Biochimica et Biophysica Acta. Gene Struct. Express.*, 1988, 949(20):125-131.
Procter, A.M. et al. "The molecular genetics of growth hormone deficiency" *Human Genetics*, 1998, 103(3):255-272.

* cited by examiner

*Primary Examiner*—Christine J Saoud
(74) *Attorney, Agent, or Firm*—Saliwanchik, Lloyd & Saliwanchik

(57) ABSTRACT

This invention relates to a novel protein, termed INSP101, herein identified as a novel splice variant of human pituitary growth hormone and to the use of this protein and nucleic acid sequences from the encoding genes in the diagnosis, prevention, and treatment of disease.

14 Claims, 8 Drawing Sheets

Figure 1: Full length INSP101 (SEQ ID NO:6) versus P01241, Pituitary growth hormone (GH-N) from *H. sapiens*:

```
Query:   1  MATGSRTSLLLAFGLLCLPWLQEGSAFPTIPLSRLFDNAMLRAHRLHQLAFDTYQEFVSS  60
            MATGSRTSLLLAFGLLCLPWLQEGSAFPTIPLSRLFDNAMLRAHRLHQLAFDTYQEF +
Sbjct:   1  MATGSRTSLLLAFGLLCLPWLQEGSAFPTIPLSRLFDNAMLRAHRLHQLAFDTYQEFEEA  60
                                                                    ***

Query:  61  W----------------GMESIPTPSNREETQQKSNLELLRISLLLIQSWLEPVQFLR  102
            +                    ESIPTPSNREETQQKSNLELLRISLLLIQSWLEPVQFLR
Sbjct:  61  YIPKEQKYSFLQNPQTSLCFSESIPTPSNREETQQKSNLELLRISLLLIQSWLEPVQFLR  120
                                *****************************************

Query: 103  SVFANSLVYGASDSNVYDLLKDLEEGIQTLMGRLEDGSPRTGQIFKQTYSKFDTNSHNDD  162
            SVFANSLVYGASDSNVYDLLKDLEEGIQTLMGRLEDGSPRTGQIFKQTYSKFDTNSHNDD
Sbjct: 121  SVFANSLVYGASDSNVYDLLKDLEEGIQTLMGRLEDGSPRTGQIFKQTYSKFDTNSHNDD  180

Query: 163  ALLKNYGLLYCFRKDMDKVETFLRIVQCRSVEGSCGF  199
            ALLKNYGLLYCFRKDMDKVETFLRIVQCRSVEGSCGF
Sbjct: 181  ALLKNYGLLYCFRKDMDKVETFLRIVQCRSVEGSCGF  217
```

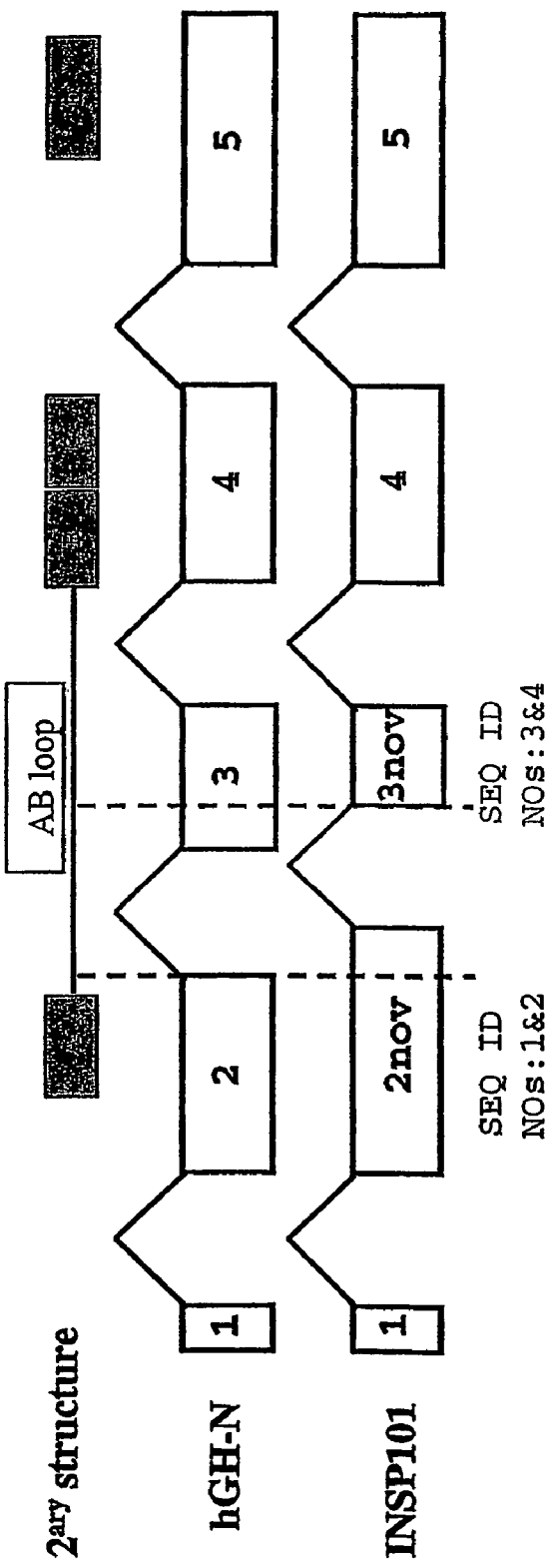

Figure 3: Predicted nucleotide sequence of INSP101 with translation. Underlined sequence denotes the predicted signal sequence

```
  1  atggctacag gctcccggac gtccctgctc ctggcttttg gcctgctctg
     m   a   t   q   s   r   t   s   l   l   l   a   f   g   l   l 51  cctgccctgg cttcaagagg gcagtgcctt cccaaccatt cccttatcca
     c   l   p   w   l   q   e   q   s   a   f   p   t   i   p   l   s 101  ggcttttga caacgctatg ctccgcgccc atcgtctgca ccagctggcc
     r   l   f   d   n   a   m   l   r   a   h   r   l   h   q   l   a 151  tttgacacct accaggagtt tgtaagctct tggggaatgg agtctattcc
     f   d   t   y   q   e   f   v   s   s   w   g   m   e   s   i 201  gacaccctcc aacagggagg aaacacaaca gaaatccaac ctagagctgc
     p   t   p   s   n   r   e   e   t   q   q   k   s   n   l   e   l 251  tccgcatctc cctgctgctc atccagtcgt ggctggagcc cgtgcagttc
     l   r   i   s   l   l   l   i   q   s   w   l   e   p   v   q   f 301  ctcaggagtg tcttcgccaa cagcctggtg tacggcgcct ctgacagcaa
     l   r   s   v   f   a   n   s   l   v   y   g   a   s   d   s 351  cgtctatgac ctcctaaagg acctagagga aggcatccaa acgctgatgg
     n   v   y   d   l   l   k   d   l   e   e   g   i   q   t   l   m 401  ggaggctgga agatggcagc ccccggactg ggcagatctt caagcagacc
     g   r   l   e   d   g   s   p   r   t   g   q   i   f   k   q   t 451  tacagcaagt tcgacacaaa ctcacacaac gatgacgcac tactcaagaa
     y   s   k   f   d   t   n   s   h   n   d   d   a   l   l   k 501  ctacgggctg ctctactgct tcaggaagga catggacaag gtcgagacat
     n   y   g   l   l   y   c   f   r   k   d   m   d   k   v   e   t 551  tcctgcgcat cgtgcagtgc cgctctgtgg agggcagctg tggcttc
     f   l   r   i   v   q   c   r   s   v   e   g   s   c   g   f
```

Figure 4: Map of plasmid pCRII-TOPO-E00974

```
Molecule:      product2, 4563 bps DNA Circular
File Name:     13686[1].cm5

Description:   Ligation of inverted NoName into PCRII-TOPO-open

Type      Start    End    Name        Description

GENE        1      336    LacZa
REGION    239      256    SP6         Sp6 promoter
GENE      943      338 C  Cds         Inserted cds (E00974)
REGION    949      337 C  Insert      Inserted PCR product
GENE      950     1201    'LacZa
REGION   1019     1038    T7          T7 promoter
GENE     1203     1617    f1          f1 ori
GENE     1951     2745    KanR        Kanamycin resistance gene
GENE     2763     3623    AmpR        Ampicillin resistance gene
GENE     3768     4441    pUC         pUC ori
```

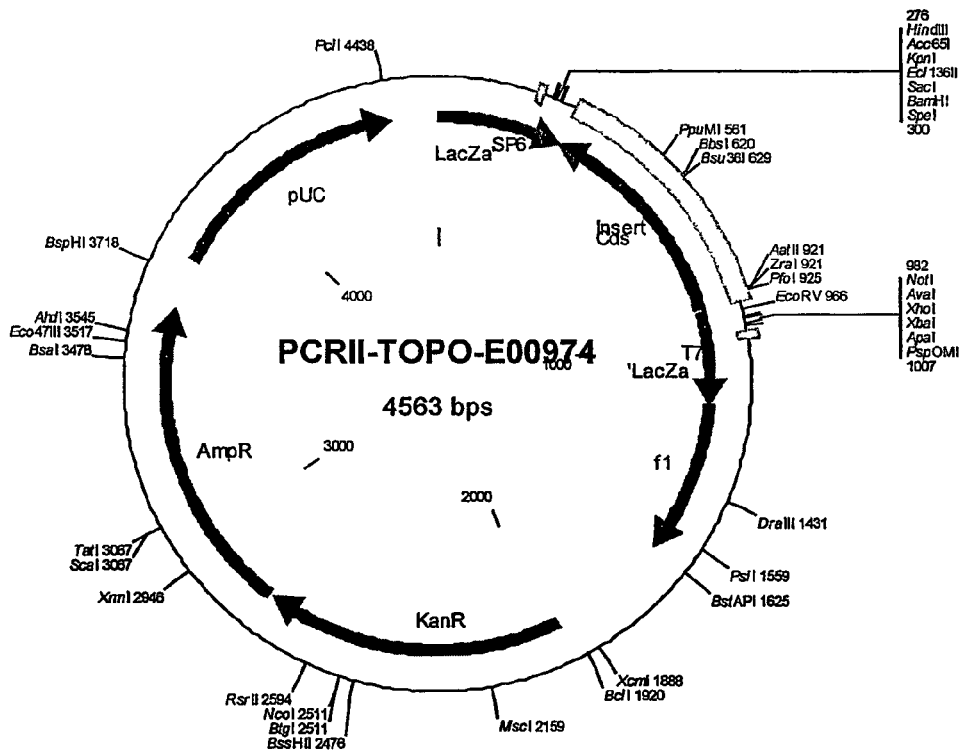

Figure 5: Alignment of INSP101 with plasmid #13686

```
top     = INSP101
bottom  = 13686
```

INSP101-B1P-5'-F
                                            ─────────────────────▶

INSP101   ATGGCTACAGGCTCCCGGACGTCCCTGCTCCTGGCTTTTGGCCTGCTCTGCCTGCCCTGG
13686     ATGGCTACAGGCTCCCGGACGTCCCTGCTCCTGGCTTTTGGCCTGCTCTGCCTGCCCTGG

INSP101   CTTCAAGAGGGCAGTGCCTTCCCAACCATTCCCTTATCCAGGCTTTTTGACAACGCTATG
13686     CTTCAAGAGGGCAGTGCCTTCCCAACCATTCCCTTATCCAGGCTTTTTGACAACGCTATG
                                                           ─────────▶ INSP101-3'-F
INSP101   CTCCGCGCCCATCGTCTGCACCAGCTGGCCTTTGACACCTACCAGGAGTTTGT------A
13686     CTCCGCGCCCATCGTCTGCACCAGCTGGCCTTTGACACCTACCAGGAGTTTAACCCCAG

INSP101   AGCTCTTGGGGAAT---GGAGTCTATTCCGACACCCTCCAACAGGGAGGAAACACAACAG
13686     ACCTCCCTCTGTTTCTCAGAGTCTATTCCGACACCCTCCAACAGGGAGGAAACACAACAG
                            ◀───── INSP101-5'-R
INSP101   AAATCCAACCTAGAGCTGCTCCGCAT................ATCCAGTCGTGGCTGGAGCCC
13686     AAATCCAACCTAGAGCTGCTCCGCATCTCCCTGCTGCTCATCCAGTCGTGGCTGGAGCCC

INSP101   GTGCAGTTCCTCAGGAGTGTCTTCGCCAACAGCCTGGTGTACGGCGCCTCTGACAGCAAC
13686     GTGCAGTTCCTCAGGAGTGTCTTCGCCAACAGCCTGGTGTACGGCGCCTCTGACAGCAAC

INSP101   GTCTATGACCTCCTAAAGGACCTAGAGGAAGGCATCCAAACGCTGATGGGGAGGCTGGAA
13686     GTCTATGACCTCCTAAAGGACCTAGAGGAAGGCATCCAAACGCTGATGGGGAGGCTGGAA

INSP101   GATGGCAGCCCCCGGACTGGGCAGATCTTCAAGCAGACCTACAGCAAGTTCGACACAAAC
13686     GATGGCAGCCCCCGGACTGGGCAGATCTTCAAGCAGACCTACAGCAAGTTCGACACAAAC

INSP101   TCACACAACGATGACGCACTACTCAAGAACTACGGGCTGCTCTACTGCTTCAGGAAGGAC
13686     TCACACAACGATGACGCACTACTCAAGAACTACGGGCTGCTCTACTGCTTCAGGAAGGAC

INSP101   ATGGACAAGGTCGAGACATTCCTGCGCATCGTGCAGTGCCGCTCTGTGGAGGGCAGCTGT
13686     ATGGACAAGGTCGAGACATTCCTGCGCATCGTGCAGTGCCGCTCTGTGGAGGGCAGCTGT
                                                    ◀───────────── INSP101-3'-R
INSP101   GGCTTC
13686     GGCTTC
          ◀─────

Figure 6: Nucleotide sequence and translation of cloned INSP101 product

```
  1  acaagtttgt acaaaaaagc aggcttcgcc accatggcta caggctcccg
                                          m  a   t  g  s 51  gacgtccctg ctcctggctt ttggcctgct ctgcctgccc tggcttcaag
      r  t  s  l  l  a   f  g  l   l  c  l  p   w  l  q 101  agggcagtgc cttcccaacc attcccttat ccaggctttt tgacaacgct
      e  g  s   a  f  p  t   i  p  l  s  r  l  f  d  n  a 151  atgctccgcg cccatcgtct gcaccagctg gcctttgaca cctaccagga
      m  l  r   a  h  r   l  h  q  l   a  f  d   t  y  q 201  gtttgtaagc tcttggggaa tggagtctat tccgacaccc tccaacaggg
      e  f  v  s   s  w  g   m  e  s   i  p  t  p   s  n  r 251  aggaaacaca acagaaatcc aacctagagc tgctccgcat ctccctgctg
      e  e  t   q  q  k  s   n  l  e   l  l  r   i  s  l  l 301  ctcatccagt cgtggctgga gcccgtgcag ttcctcagga gtgtcttcgc
      l  i  q   s  w  l   e  p  v  q   f  l  r   s  v  f 351  caacagcctg gtgtacggcg cctctgacag caacgtctat gacctcctaa
      a  n  s  l   v  y  g   a  s  d  s   n  v  y   d  l  l 401  aggacctaga ggaaggcatc caaacgctga tggggaggct ggaagatggc
      k  d  l   e  e  g  i   q  t  l   m  g  r   l  e  d  g 451  agcccccgga ctgggcagat cttcaagcag acctacagca agttcgacac
      s  p  r   t  g  q   i  f  k  q   t  y  s   k  f  d 501  aaactcacac aacgatgacg cactactcaa gaactacggg ctgctctact
      t  n  s  h   n  d  d   a  l  l   k  n  y  g   l  l  y 551  gcttcaggaa ggacatggac aaggtcgaga cattcctgcg catcgtgcag
      c  f  r   k  d  m  d   k  v  e   t  f  l   r  i  v  q 601  tgccgctctg tggagggcag ctgtggcttc caccatcacc atcaccattg
      c  r  s   v  e  g   s  c  g  f   h  h  h   h  h  h 651  aaacccagct ttcttgtaca aagtggt
```

Figure 7: Map of pENTR-INSP101-6HIS

```
Molecule:      pENTR-INSP101-6HIS,  3171 bps DNA Circular
File Name:     pENTR-INSP101-6HIS-V1.cm5,  dated 21 Nov 2003

Description:   Ligation of Blb2-orf.seq* into pDONR221*

Type      Start    End      Name          Description

REGION    295      268   C  rrnB T2       transcription termination sequence
REGION    470      427   C  rrnB T1       transcription termination sequence
REGION    537      552      M13F          forward primer
REGION    570      651      attL1
GENE      677      1291     INSP101-6HIS
REGION    1306     1394     attL2
REGION    1452     1436  C  M13 R         reverse primer
GENE      1565     2374     Kan r
GENE      2495     3168     pUC ori
```

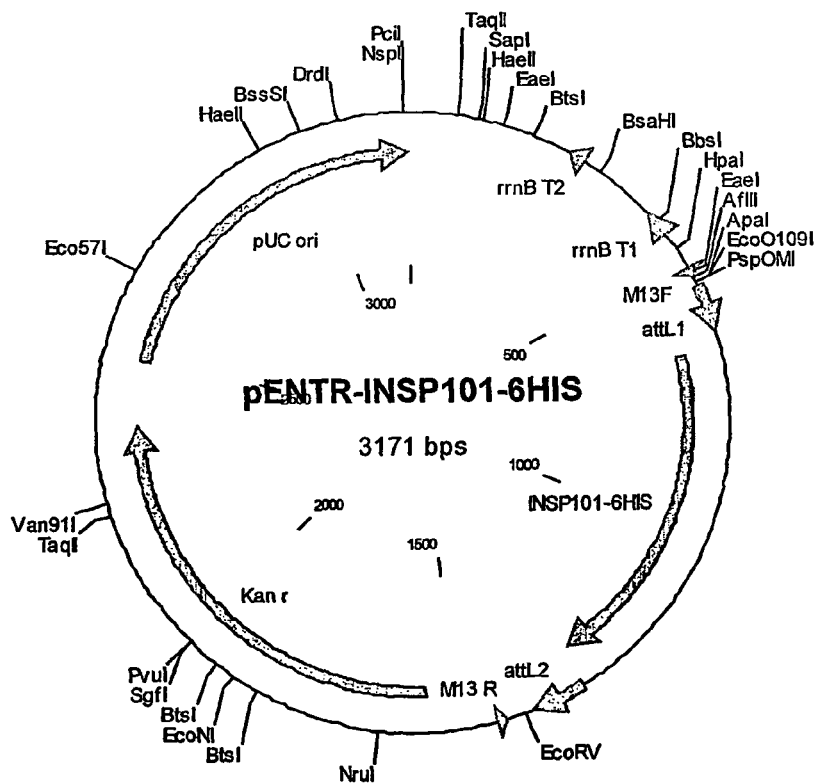

Figure 8: Map of pEAK12d-INSP101-6HIS

```
Molecule:     pEAK12d-INSP101-6HIS-V1,   7564 bps DNA Circular
File Name:    pEAK12d-INSP101-6HIS-V1.cm5,  dated 17 Jul 2003

Description:  pEAK12 DES with two recombination sites attR1 and attR2
between which the cDNA is inserted
```

| Type   | Start | End   |   | Name         | Description    |
|--------|-------|-------|---|--------------|----------------|
| REGION | 2     | 595   |   | pmb-ori      |                |
| GENE   | 596   | 1519  |   | Amp          |                |
| REGION | 1690  | 2795  |   | EF-1alpha    |                |
| REGION | 2703  | 2722  |   | peak12-F     | forward primer |
| REGION | 2855  | 2874  |   | attB1        |                |
| GENE   | 2888  | 3502  |   | INSP101-6HIS |                |
| REGION | 3510  | 3531  |   | attB2        |                |
| REGION | 3538  | 3966  |   | 'A           | poly A/splice  |
| REGION | 3652  | 3633  | C | peak12-R     | reverse primer |
| GENE   | 4585  | 3967  | C | PUR          | PUROMYCIN      |
| REGION | 4809  | 4586  | C | tK           | tK promoter    |
| REGION | 5304  | 4810  | C | Ori P        |                |
| GENE   | 7356  | 5304  | C | EBNA-1       |                |
| REGION | 7357  | 7556  |   | sv40         |                |

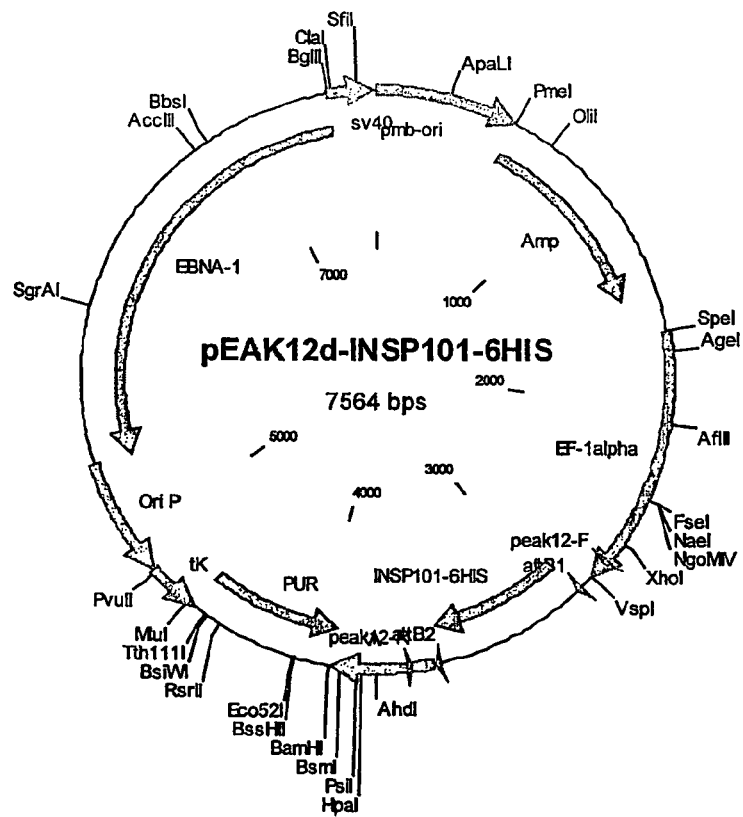

SPLICE VARIANT OF THE HUMAN PITUITARY GROWTH HORMONE

CROSS-REFERENCE TO RELATED APPLICATION

This application is the National Stage of International Application Number PCT/GB2003/005295, filed Dec. 5, 2003, which is hereby incorporated by reference herein in its entirety, including any figures, tables, nucleic acid sequences, amino acid sequences, or drawings.

This invention relates to a novel protein, termed INSP101, herein identified as a novel splice variant of human pituitary growth hormone (GH-N; P01241) and to the use of this protein and nucleic acid sequences from the encoding gene in the diagnosis, prevention and treatment of disease. The variant has an altered A-B loop and is therefore predicted to possess altered receptor binding properties.

All publications, patents and patent applications cited herein are incorporated in full by reference.

BACKGROUND

The process of drug discovery is presently undergoing a fundamental revolution as the era of functional genomics comes of age. The term "functional genomics" applies to an approach utilising bioinformatics tools to ascribe function to protein sequences of interest. Such tools are becoming increasingly necessary as the speed of generation of sequence data is rapidly outpacing the ability of research laboratories to assign functions to these protein sequences.

As bioinformatics tools increase in potency and in accuracy, these tools are rapidly replacing the conventional techniques of biochemical characterisation. Indeed, the advanced bioinformatics tools used in identifying the present invention are now capable of outputting results in which a high degree of confidence can be placed.

Various institutions and commercial organisations are examining sequence data as they become available and significant discoveries are being made on an on-going basis. However, there remains a continuing need to identify and characterise further genes and the polypeptides that they encode, as targets for research and for drug discovery.

Alternative pre-mRNA splicing is a major cellular process by which functionally diverse proteins can be generated from the primary transcript of a single gene, often in tissue specific patterns.

Experimentally, splice variants are identified by the fortuitous isolation and subsequent sequencing of variant mRNAs. However, this experimental approach has not been exhaustively completed for the human transcriptome (since this would require systematic isolation and sequencing of all mRNAs from all human tissues under all possible environmental conditions) and due to this experimental limitation there remains a large number of splice variants which have yet to be identified.

We have used proprietary bioinformatic approaches to perform a purposeful, directed search for the existence of splice variants of the human growth hormone gene. By this method the limited data set of experimentally known splice variants can be extended to a much larger set of predicted splice variants.

Endocrine Hormones

Hormones regulate a wide variety of physiological functions encompassing intermediary metabolism, growth and cell differentiation. They have two fundamental mechanisms of action, depending on their physical chemical characteristics. The lipophilic steroid hormones and thyroid hormones are hydrophobic and act primarily intracellularly, modulating gene transcription, whereas the peptide hormones such as adrenaline and melatonin are hydrophilic and act at the cell membrane, triggering a cascade of signal transduction events leading to intracellular regulatory effects (Lodish et al. (1995) *Molecular Cell Biology*, Scientific American Books Inc., New York, N.Y., pp. 856-864.

Hormones are produced in specialised cells of the endocrine glands and reach their target cells by way of the blood circulation. The steroid hormones are derived from cholesterol by a series of enzymatic reactions that take place in the cytosol and in mitochondria of primarily cells of the adrenal cortex, ovary, and testis. In some cases the steroid hormone must be subjected to modification in the target tissue, either to be activated or to produce a more active derivative. Most of the peptide hormones are synthesized in the form of precursor proteins (prohormones) and are stored in the endocrine cell. Before being released into the circulation, the prohormone is cleaved to the active hormone. Several hormones (primarily steroid hormones and thyroid hormones) are transported in the circulation while bound to specific binding proteins. These proteins serve as hormone depots, releasing the hormone when needed and also protecting it from rapid inactivation.

Because of the central nature of hormones in the general physiology of *H. sapiens*, the dys-regulation of hormonal function has been shown to play a role in many disease processes, including, but not limited to oncology (Sommer S. and Fuqua S. A. (2001) Semin Cancer Biol. October;11 (5): 339-52, Bartucci M., Morelli C., Mauro L, Ando S., and Surmacz E. (2001) Cancer Res. September 15;61 (18):6747-54, Oosthuizen G. M., Joubert G., and du Toit R. S. (2001) S. Afr. Med. J. July;91 (7):576-79, Nickerson T., Chang F., Lorimer D., Smeekens S. P., Sawyers C. L., and Pollak M. (2001) Cancer Res. August 15;61 (16):6276-80), cardiovascular disease (Liu Y., Ding J., Bush T. L., Longenecker J. C., Nieto F. J., Golden S. H., and Szklo M. (2001) Am. J. Epidemiol. September 15;154 (6):489-94), metabolic diseases (Flyvbjerg A. (2001) Growth Horm. IGF Res. June;11 Suppl. A:S115-9, Diamond T., Levy S., Smith A., Day P. and Manoharan A. (2001) Intern. Med. J. July;31 (5):272-8, Toprak S., Yonem A., Cakir B., Guler S., Azal O., Ozata M., and Corakci A. (2001) Horm. Res.;55 (2):65-70), inflammation (McEvoy A. N., Bresnihan B., FitzGerald O., and Murphy E. P. (2001) Arthritis Rheum. August;44 (8):1761-7, Lipsett P. A. (2001) Crit. Care Med. August;29 (8):16424) and CNS related diseases (Bowen R. L. (2001) JAMA. August 15;286 (7):790-1).

Growth Hormone Family

Growth hormone is a member of a family of polypeptide hormones that share structural similarities and biological activities and are produced in the pituitary glands of all vertebrates and the placentae of some mammals. Family members include pituitary prolactin, placental lactogens (also called chorionic somatomammotropins in humans [hCS]), prolactin-related proteins in ruminants and rodents, proliferins in mice, and somatolactin in fish.

The genes that encode most members of the GH family comprise five exons and four introns and appear to have arisen by duplication of a single ancestral gene prior to the appearance of the vertebrates. Splicing and processing variants have been described for several members of the family.

The human GH-related gene family located on chromosome 17q22-24 consists of a gene cluster of highly sequence-conserved genes and a single prolactin gene on chromosome 6 (Owerbach D. et al. Science 1981). The gene cluster includes five structural genes, two GH and three CS genes, whose expression is tissue specific: hGH-N (N=normal), hGH-V (V=variant), human chorionic somatomammotropin hormone-like (hCS-L), human chorionic somatomammotropin A and B (hCS-A and hCS-B) (Misra-Press, A et al. JBC 1994; Boguszewski C. et al. JBC 1998).

The GH-related family of proteins has shared structural similarities since their tertiary structure form four $\alpha$-helices, also known as a four antiparallel helix bundle. The $\alpha$-helices are tightly packed and arranged in an antiparallel up-up-down-down orientation, with two long loops linking the parallel pairs.

The hGH/hCS gene family is important in the regulation of maternal and fetal metabolism and the growth and development of the fetus. During pregnancy, pituitary GH (hGH-N) expression in the mother is suppressed; and hGH-V, a GH variant expressed by the placenta, becomes the predominant GH in the mother. hCS, which is the product of the hCS-A and hCS-B genes, is secreted into both the maternal and fetal circulations after the sixth week of pregnancy. hGH-V and hCS act in concert in the mother to stimulate insulin-like growth factor (IGF) production and modulate intermediary metabolism, resulting in an increase in the availability of glucose and amino acids to the fetus. In the fetus, hCS acts via lactogenic receptors and possibly a unique CS receptor to modulate embryonic development, regulate intermediary metabolism and stimulate the production of IGFs, insulin, adrenocortical hormones and pulmonary surfactant. hGH-N, which is expressed by the fetal pituitary, has little or no physiological actions in the fetus until late in pregnancy due to the lack of functional GH receptors on fetal tissues. hGH-V, which is also a potent somatogenic hormone, is not released into the fetus. Taken together, studies of the hGH/hCS gene family during pregnancy reveal a complex interaction of the hormones with one another and with other growth factors. Additional investigations are necessary to clarify the relative roles of the family members in the regulation of fetal growth and development and the factors that modulate the expression of the genes. (Handwerger S. & Freemark M. J., Pediatr. Endocrinol. Metab. 2000 April;13 (4):343-56).

Human growth hormone, also known as somatotropin, is a protein hormone of about 190 amino acids that is synthesized and secreted by cells called somatotrophs in the anterior pituitary. It is a major participant in control of several complex physiologic processes, including growth and metabolism. Growth hormone is also of considerable interest as a drug used in both humans and animals.

Growth hormone has two distinct types of effects. Direct effects are the result of growth hormone binding its receptor on target cells. Fat cells (adipocytes), for example, have growth hormone receptors, and growth hormone stimulates them to break down triglyceride and suppresses their ability to take up and accumulate circulating lipids. Indirect effects are mediated primarily by insulin-like growth factor-1 (IGF-1). The major role of growth hormone in stimulating body growth is to stimulate the liver and other tissues to secrete IGF-1. A majority of the growth promoting effects of growth hormone is actually due to IGF-1 acting on its target cells. For example, IGF-1 stimulates proliferation of chondrocytes (cartilage cells), resulting in bone growth. Growth hormone also has important effects on protein, lipid and carbohydrate metabolism. In some cases, a direct effect of growth hormone has been clearly demonstrated, in others, IGF-1 is thought to be the critical mediator, and some cases it appears that both direct and indirect effects are at play.

In addition to its complex effects on growth, states of both growth hormone deficiency and excess provide very visible testaments to the role of this hormone in normal physiology. Such disorders can reflect lesions in either the hypothalamus, the pituitary or in target cells. A deficiency state can result not only from a deficiency in production of the hormone, but in the target cell's response to the hormone.

Clinically, deficiency in growth hormone or receptor defects are as growth retardation or dwarfism. The manifestation of growth hormone deficiency depends upon the age of onset of the disorder and can result from either heritable or acquired disease.

The effect of excessive secretion of growth hormone is also very dependent on the age of onset and is seen as two distinctive disorders. Giantism is the result of excessive growth hormone secretion that begins in young children or adolescents. It is a very rare disorder, usually resulting from a tumour of somatotropes.

Acromegaly results from excessive secretion of growth hormone in adults. The onset of this disorder is typically insideous. Clinically, an overgrowth of bone and connective tissue leads to a change in appearance that might be described as having "coarse features". The excessive growth hormone and IGF-1 also lead to metabolic derangements, including glucose intolerance.

Growth hormone purified from human cadaver pituitaries has long been used to treat children with severe growth retardation. More recently, the availability of recombinant growth hormone has lead to several other applications to human and animal populations. For example, human growth hormone is commonly used to treat children of pathologically short stature. The role of growth hormone in normal aging remains poorly understood, but some of the cosmetic symptoms of aging appear to be amenable to growth hormone therapy. Growth hormone is currently approved and marketed for enhancing milk production in dairy cattle; another application of growth hormone in animal agriculture is treatment of growing pigs with porcine growth hormone. Such treatment has been demonstrated to significantly stimulate muscle growth and reduce deposition of fat.

As growth hormone plays such a key role in cellular processes, the study of this moiety and its method of regulation are of key interest. The identification of splice variants of this hormone would be of great scientific importance.

The Invention

The invention is based on the discovery that the INSP101 protein is a novel splice variant of human pituitary growth hormone (GH-N; P01241).

In one embodiment of the first aspect of the invention, there is provided a polypeptide which:
(i) comprises the amino acid sequence as recited in SEQ ID NO:2, SEQ ID NO:4, SEQ ID NO: 6, SEQ ID NO:8 or SEQ ID NO:10;
(ii) is a fragment thereof which functions as a growth hormone, or has an antigenic determinant in common with a polypeptide according to (i); or
(iii) is a functional equivalent of (i) or (ii).

Preferably, the polypeptide according to this first embodiment of this first aspect of the invention:
(i) comprises the amino acid sequence as recited in SEQ ID NO:8 or SEQ ID NO:10;
(ii) is a fragment thereof which functions as a growth hormone, or has an antigenic determinant in common with a polypeptide according to (i); or
(iii) is a functional equivalent of (i) or (ii).

According to a second embodiment of this first aspect of the invention, there is provided a polypeptide which consists of the amino acid sequence as recited in SEQ ID NO:2, SEQ ID NO:4, SEQ ID NO: 6, SEQ ID NO:8 or SEQ ID NO:10.

The polypeptide having the sequence recited in SEQ ID NO:2 is referred to hereafter as "the INSP101 exon 2nov polypeptide". The polypeptide having the sequence recited in SEQ ID NO:4 is referred to hereafter as "the INSP101 exon 3nov polypeptide". The polypeptide having the sequence recited in SEQ ID NO:6 is referred to hereafter as "the INSP101 contiguous exon 2nov-3nov polypeptide". The polypeptide having the sequence recited in SEQ ID NO:8 is referred to hereafter as "the INSP101 full length polypeptide". The polypeptide having the sequence recited in SEQ ID NO:10 is referred to hereafter as "the INSP101 full length mature polypeptide".

FIG. 2 compares the splicing pattern of P01241, pituitary growth hormone (GH-N) from *H. sapiens* with the splicing pattern of the novel splice variant INSP101. As is clear from this figure, the protein comprises 5 separate exons. The INSP101 exon 2nov polypeptide and the INSP101 exon 3nov polypeptide are alternative exons produced by alternative splicing; the splice variant has an extended exon2 (2nov) and a truncated exon3 (3nov).

The diagram also displays the main secondary structure elements of pituitary growth hormone (GH-N). GH-N is composed of four alpha helices (A, B, C and D), and of particular importance is the "A-B loop" which connects helix A to helix B. The A-B loop is a critical component of the GH-N interaction surface which binds the Growth Hormone receptor (Wells J A, PNAS vol. 93, pp. 1-6 1996, "Binding in the growth hormone receptor complex"). It is evident that the novel splice variant INSP101 has new residues inserted in the A-B loop (due to the extension of exon 2). Similarly, the truncation of exon 3 will lead to the removal of some GH-N residues in the A-B loop. Thus INSP101 differs from GH-N principally in the composition of the A-B loop, and since this loop is a primary determinant in binding to the growth hormone receptor, INSP101 is predicted to exhibit altered receptor binding properties (in terms of binding affinity and/or receptor selectivity).

The term "INSP101 polypeptides" as used herein includes polypeptides comprising or consisting of the INSP101 exon 2nov polypeptide, the INSP101 exon 3nov polypeptide, the INSP101 contiguous exon 2nov-3nov polypeptide, the INSP101 full length polypeptide, and the INSP101 full length mature polypeptide.

By "functions as a growth hormone" we refer to polypeptides that comprise amino acid sequence or structural features that can be identified as conserved features within human growth hormones, such that the polypeptide's activity is not substantially affected detrimentally in comparison to the function of the full length wild type polypeptide. For example, a number of different assays may be used to determine the effects of human growth hormones on binding (see, for example, Well J. A. PNAS Vol. 93 pp. 1-6, 1996), including the use of monoclonal antibodies to precipitate 1:1 complexes of growth hormone and receptor, and the hGH-induced dimerization of hGHbp molecules in solution by the quenching of a fluorescent tag placed near the C terminus of the hGHbp (see Well J. A. PNAS Vol. 93 pp. 1-6, 1996). [hGHbp=extracellular domain of GH receptor]

Several assays are available that allow the detection of growth hormone activity. These include the following metabolic endocrinology assays:

i) Differentiation to Adipocyte Assay:

Inhibition of adipocyte differentiation is an in vitro model for reduction of adipose mass believed to be important in reducing insulin resistance in diseases such as diabetes and Polycystic Ovary Syndrome (PCOS). The goal is to identify protein(s) that inhibit differentiation of pre-adipocytes to adipocytes. The 3T3-L1 mouse preadipocyte cell line is induced to differentiate to adipocytes with insulin+IBMX. The finding that differentiation is inhibited by TNFα+cyclohexamide is used as a positive control.

ii) Tritiated Glucose Uptake (3T3 L1):

The goal is to identify protein(s) that stimulate glucose uptake as a model for insulin-resistance in adipose during diabetes or PCOS. Adipocytes used are mouse 3T3-L1 preadipocytes that have been differentiated.

iii) Tritiated Glucose Uptake (Primary Human Adipocytes):

The goal is to identify protein(s) that stimulate glucose uptake as a model for insulin-resistance in adipose during diabetes or PCOS. Primary human adipocytes are used.

iv) Tritiated Glucose Update (Primary Human Skeletal Muscle Cells):

The goal is to identify protein(s) that stimulate glucose uptake as a model for insulin-resistance in muscle tissue during diabetes or PCOS. Primary human skeletal muscle cells are differentiated into myotubes and then used in the assay.

In a second aspect, the invention provides a purified nucleic acid molecule which encodes a polypeptide of the first aspect of the invention.

In a first embodiment of this aspect of the invention, the purified nucleic acid molecule comprises the nucleic acid sequence as recited in SEQ ID NO:1 (encoding the INSP101 exon 2nov polypeptide), SEQ ID NO:3 (encoding the INSP101 exon 3nov polypeptide), SEQ ID NO:5 (encoding the INSP101 contiguous exon 2nov-3nov polypeptide), SEQ ID NO:7 (encoding the INSP101 full length polypeptide), or SEQ ID NO:9 (encoding the INSP101 full length mature polypeptide) or is a redundant equivalent or fragment of any one of these sequences.

The invention further provides that the purified nucleic acid molecule consists of the nucleic acid sequence as recited in SEQ ID NO:1 (encoding the INSP101 exon 2nov polypeptide), SEQ ID NO:3 (encoding the INSP101 exon 3nov polypeptide), SEQ ID NO:5 (encoding the INSP101 contiguous exon 2nov-3nov polypeptide), SEQ ID NO:7 (encoding the INSP101 full length polypeptide), or SEQ ID NO:9 (encoding the INSP101 full length mature polypeptide), or is a redundant equivalent or fragment of any one of these sequences.

The coding sequence encoding wild type pituitary human growth hormone, NM_000515, is specifically excluded from the scope of the present invention.

In a third aspect, the invention provides a purified nucleic acid molecule which hybridizes under high stringency conditions with a nucleic acid molecule of the second aspect of the invention.

In a fourth aspect, the invention provides a vector, such as an expression vector, that contains a nucleic acid molecule of the second or third aspect of the invention.

In a fifth aspect, the invention provides a host cell transformed with a vector of the fourth aspect of the invention.

In a sixth aspect, the invention provides a ligand which binds specifically to growth hormones of the first aspect of the invention. Preferably, the ligand inhibits the function of a polypeptide of the first aspect of the invention which is a growth hormone. Ligands to a polypeptide according to the invention may come in various forms, including natural or modified substrates, enzymes, receptors, small organic molecules such as small natural or synthetic organic molecules of up to 2000 Da, preferably 800 Da or less, peptidomimetics, inorganic molecules, peptides, polypeptides, antibodies, structural or functional mimetics of the aforementioned.

In a seventh aspect, the invention provides a compound that is effective to alter the expression of a natural gene which encodes a polypeptide of the first aspect of the invention or to regulate the activity of a polypeptide of the first aspect of the invention.

A compound of the seventh aspect of the invention may either increase (agonise) or decrease (antagonise) the level of expression of the gene or the activity of the polypeptide.

Importantly, the identification of the function of the INSP101 polypeptide allows for the design of screening methods capable of identifying compounds that are effective in the treatment and/or diagnosis of disease. Ligands and compounds according to the sixth and seventh aspects of the invention may be identified using such methods. These methods are included as aspects of the present invention.

In an eighth aspect, the invention provides a polypeptide of the first aspect of the invention, or a nucleic acid molecule of the second or third aspect of the invention, or a vector of the fourth aspect of the invention, or a ligand of the sixth aspect of the invention, or a compound of the seventh aspect of the invention, for use in therapy or diagnosis of a disease in which human growth hormone is implicated. Such diseases and disorders may include reproductive disorders, preganancy disorder, such as gestational trophoblastic disease, developmental disorders such as Silver-Russell syndrome, growth disorders, growth hormone deficiency, Cushing's disease, endocrine disorders, cell proliferative disorders, including neoplasm, carcinoma, pituitary tumour, ovary tumour, melanoma, lung, colorectal, breast, pancreas, head and neck, placental site trophoblastic tumor, adenocarcinoma, choriocarcinoma, osteosarcoma and other solid tumours; angiogeneisis, myeloproliferative disorders; autoimmune/inflammatory disorders; cardiovascular disorders; neurological disorders, pain; metabolic disorders including diabetes mellitus, osteoporosis, and obesity, cachexia, AIDS, renal disease; lung injury; ageing; infections including viral infection, bacterial infection, fungal infection and parasitic infection, and other pathological conditions. Preferably, the disease is one in which endocrine function, particularly growth hormones are implicated (see, for example, Arato G., Fulop V., Degrell P., Szigetvari I. Pathol. Oncol. Res. 2000 6 (4):292-4; Hitchins M. P., Stanier P., Preece M. A. and Moore G E., J. Med. Genet. 2001 December 38 (12):810-9; Rhoton-Vlasak A., Wagner J. M., Rutgers J. L., Baergen R. N., Young R. H., Roche P. C., Plummer T. B. and Gleich G. J., Hum Pathol 1998 March 29 (3):280-8; Llovera M., Pichard C., Bernichtein S., Jeay S., Touraine P., Kelly P. A. and Goffin V., Oncogene, 2000 September 28 19 (41):4695-705; Savage M. O., Scommegna S., Carroll P. V., Ho J. T., Monson J. P., Besser G. M. and Grossman A B., Horm. Res. 2002 58 Suppl 1:39-43; Aimaretti G., Corneli G., Bellone S., Baffoni C., Camanni F. and Ghigo E., J. Pediatr. Endocrinol. Metab. 2001 14 Suppl 5:1233-42; Berger P., Untergasser G., Hermann M., Hittmair A., Madersbacher S. and Dirnhofer S., Hum. Pathol. 1999 October 30 (10):1201-6; Hamilton J., Chitayat D., Blaser S., Cohen L. E., Phillips J. A. 3rd and Daneman D., Am. J. Med. Genet. 1998 November 2 80 (2):128-32; Gonzalez-Rodriguez E., Jaramillo-Rangel G. and Barrera-Saldana H. A., Am. J. Med. Genet. 1997 Nov. 12 72 (4):399-402; Perez Jurado L. A., Argente J., Barrios V., Pozo J., Munoz M. T., Hernandez M. and Francke U., J. Pediatr. Endocrinol. Metab. 1997 March-April 10 (2):185-90; Saeger W. and Lubke D., Endocr. Pathol. 1996 Spring 7 (1):21-35; Conzemius M. G., Graham J. C., Haynes J. S. and Graham C. A., Am. J. Vet. Res. 2000 June 61 (6):646-50; Bartlett D. L., Charland S., Torosian M. H., Cancer 1994 March 1 73 (5):1499-504). These molecules may also be used in the manufacture of a medicament for the treatment of such disorders.

In a ninth aspect, the invention provides a method of diagnosing a disease in a patient, comprising assessing the level of expression of a natural gene encoding a polypeptide of the first aspect of the invention or the activity of a polypeptide of the first aspect of the invention in tissue from said patient and comparing said level of expression or activity to a control level, wherein a level that is different to said control level is indicative of disease. Such a method will preferably be carried out in vitro. Similar methods may be used for monitoring the therapeutic treatment of disease in a patient, wherein altering the level of expression or activity of a polypeptide or nucleic acid molecule over the period of time towards a control level is indicative of regression of disease.

A preferred method for detecting polypeptides of the first aspect of the invention comprises the steps of: (a) contacting a ligand, such as an antibody, of the sixth aspect of the invention with a biological sample under conditions suitable for the formation of a ligand-polypeptide complex; and (b) detecting said complex.

A number of different methods according to the ninth aspect of the invention exist, as the skilled reader will be aware, such as methods of nucleic acid hybridization with short probes, point mutation analysis, polymerase chain reaction (PCR) amplification and methods using antibodies to detect aberrant protein levels. Similar methods may be used on a short or long term basis to allow therapeutic treatment of a disease to be monitored in a patient. The invention also provides kits that are useful in these methods for diagnosing disease.

In a tenth aspect, the invention provides for the use of the polypeptides of the first aspect of the invention as a growth hormone or as a modulator of growth hormone activity. Suitable uses of the polypeptides of the invention as growth hormones include use as a regulator of cellular growth, metabolism or differentiation, use as part of a receptor/ligand pair and use as a diagnostic marker for a physiological or pathological condition. As mentioned above, growth hormone stimulates the breakdown of triglyceride in adipocytes. Human growth hormone also stimulates body growth by stimulating the liver to secrete IGF-1. This, in turn, results in proliferation of chondrocytes, resulting in bone growth. Growth hormone also has effects on metabolism. The administration of growth hormone is a known treatment for dwarfism. It is also known to be used to increase milk production in dairy cattle and to increase growth in pigs. All of these utilities may be exploited by the polypeptides of the invention. Furthermore, antagonists to polypeptides of the invention may be used to treat the overproduction of growth hormone, which can result in giantism.

As discussed above, a number of different assays may be used to determine the effects of human Growth Hormones on binding (see, for example, Well J. A. PNAS Vol. 93 pp. 1-6, 1996), including the use of monoclonal antibodies to precipitate 1:1 complexes of growth hormone and receptor, and the hGH-induced dimerization of hGHbp molecules in solution by the quenching of a fluorescent tag placed near the C terminus of the hGHbp (see Well J. A. PNAS Vol. 93 pp. 1-6, 1996). [hGHbp=extracellular domain of GH receptor]

In an eleventh aspect, the invention provides a pharmaceutical composition comprising a polypeptide of the first aspect of the invention, or a nucleic acid molecule of the second or third aspect of the invention, or a vector of the fourth aspect of the invention, or a ligand of the sixth aspect of the invention, or a compound of the seventh aspect of the invention, in conjunction with a pharmaceutically-acceptable carrier.

In a twelfth aspect, the present invention provides a polypeptide of the first aspect of the invention, or a nucleic acid molecule of the second or third aspect of the invention, or a vector of the fourth aspect of the invention, or a ligand of the sixth aspect of the invention, or a compound of the seventh aspect of the invention, for use in therapy or diagnosis.

These molecules may also be used in the manufacture of a medicament for the treatment of a disease.

In a thirteenth aspect, the invention provides a method of treating a disease in a patient comprising administering to the patient a polypeptide of the first aspect of the invention, or a nucleic acid molecule of the second or third aspect of the invention, or a vector of the fourth aspect of the invention, or a ligand of the sixth aspect of the invention, or a compound of the seventh aspect of the invention.

For diseases in which the expression of a natural gene encoding a polypeptide of the first aspect of the invention, or in which the activity of a polypeptide of the first aspect of the invention, is lower in a diseased patient when compared to the level of expression or activity in a healthy patient, the polypeptide, nucleic acid molecule, ligand or compound administered to the patient should be an agonist. Conversely, for diseases in which the expression of the natural gene or activity of the polypeptide is higher in a diseased patient when compared to the level of expression or activity in a healthy patient, the polypeptide, nucleic acid molecule, ligand or compound administered to the patient should be an antagonist. Examples of such antagonists include antisense nucleic acid molecules, ribozymes and ligands, such as antibodies.

In a fourteenth aspect, the invention provides transgenic or knockout non-human animals that have been transformed to express higher, lower or absent levels of a polypeptide of the first aspect of the invention. Such transgenic animals are very useful models for the study of disease and may also be used in screening regimes for the identification of compounds that are effective in the treatment or diagnosis of such a disease.

A summary of standard techniques and procedures which may be employed in order to utilise the invention is given below. It will be understood that this invention is not limited to the particular methodology, protocols, cell lines, vectors and reagents described. It is also to be understood that the terminology used herein is for the purpose of describing particular embodiments only and it is not intended that this terminology should limit the scope of the present invention. The extent of the invention is limited only by the terms of the appended claims.

Standard abbreviations for nucleotides and amino acids are used in this specification.

The practice of the present invention will employ, unless otherwise indicated, conventional techniques of molecular biology, microbiology, recombinant DNA technology and immunology, which are within the skill of those working in the art.

Such techniques are explained fully in the literature. Examples of particularly suitable texts for consultation include the following: Sambrook Molecular Cloning; A Laboratory Manual, Second Edition (1989); DNA Cloning, Volumes I and II (D. N Glover ed. 1985); Oligonucleotide Synthesis (M. J. Gait ed. 1984); Nucleic Acid Hybridization (B. D. Hames & S. J. Higgins eds. 1984); Transcription and Translation (B. D. Hames & S. J. Higgins eds. 1984); Animal Cell Culture (R. I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Immunochemical Methods in Cell and Molecular Biology (Mayer and Walker, eds. 1987, Academic Press, London); Scopes, (1987) Protein Purification: Principles and Practice, Second Edition (Springer Verlag, N.Y.); and Handbook of Experimental Immunology, Volumes I-IV (D. M. Weir and C. C. Blackwell eds. 1986).

As used herein, the term "polypeptide" includes any peptide or protein comprising two or more amino acids joined to each other by peptide bonds or modified peptide bonds, i.e. peptide isosteres. This term refers both to short chains (peptides and oligopeptides) and to longer chains (proteins).

The polypeptide of the present invention may be in the form of a mature protein or may be a pre-, pro- or preproprotein that can be activated by cleavage of the pre-, pro- or prepro-portion to produce an active mature polypeptide. In such polypeptides, the pre-, pro- or prepro-sequence may be a leader or secretory sequence or may be a sequence that is employed for purification of the mature polypeptide sequence.

The polypeptide of the first aspect of the invention may form part of a fusion protein. For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature polypeptide may be fused with another compound, such as a compound to increase the half-life of the polypeptide (for example, polyethylene glycol).

Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

Modifications can occur anywhere in a polypeptide, including the peptide backbone, the amino acid side-chains and the amino or carboxyl termini. In fact, blockage of the amino or carboxyl terminus in a polypeptide, or both, by a covalent modification is common in naturally-occurring and synthetic polypeptides and such modifications may be present in polypeptides of the present invention.

The modifications that occur in a polypeptide often will be a function of how the polypeptide is made. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell.

The polypeptides of the present invention can be prepared in any suitable manner. Such polypeptides include isolated naturally-occurring polypeptides (for example purified from cell culture), recombinantly-produced polypeptides (including fusion proteins), synthetically-produced polypeptides or polypeptides that are produced by a combination of these methods.

The functionally-equivalent polypeptides of the first aspect of the invention may be polypeptides that are homologous to the INSP101 polypeptides. Two polypeptides are said to be "homologous", as the term is used herein, if the sequence of one of the polypeptides has a high enough degree of identity or similarity to the sequence of the other polypeptide. "Identity" indicates that at any particular position in the aligned sequences, the amino acid residue is identical between the sequences. "Similarity" indicates that, at any particular position in the aligned sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Homologous polypeptides therefore include natural biological variants (for example, allelic variants or geographical variations within the species from which the polypeptides are derived) and mutants (such as mutants containing amino acid substitutions, insertions or deletions) of the INSP101 polypeptides. Such mutants may include polypeptides in which one or more of the amino acid residues are substituted with a conserved or non-conserved amino acid residue (preferably a conserved amino acid residue) and such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions. Such mutants also include polypeptides in which one or more of the amino acid residues includes a substituent group.

Typically, greater than 30% identity between two polypeptides is considered to be an indication of functional equivalence. Preferably, functionally equivalent polypeptides of the first aspect of the invention have a degree of sequence identity with the INSP101 polypeptide, or with active fragments thereof, of greater than 90% over the full length of the INSP101 sequence. More preferred polypeptides have degrees of identity of greater than 92%, 95%, 98% or 99% over the fill length of the INSP101 sequence, respectively.

The functionally-equivalent polypeptides of the first aspect of the invention may also be polypeptides which have been identified using one or more techniques of structural alignment. For example, the Inpharmatica Genome Threader™ technology that forms one aspect of the search tools used to generate the Biopendium search database may be used (see co-pending International Patent Application No. PCT/GB01/01105) to identify polypeptides of presently-unknown function which, while having low sequence identity as compared to the INSP101 polypeptide, are predicted to be growth hormone proteins, said method utilising a polypeptide of the first aspect of the invention, by virtue of sharing significant structural homology with the INSP101 polypeptide sequences. By "significant structural homology" is meant that the Inpharmatica Genome Threader™ predicts two proteins to share structural homology with a certainty of at least 10% and above.

The polypeptides of the first aspect of the invention also include fragments of the INSP101 polypeptides and fragments of the functional equivalents of the INSP101 polypeptides, provided that those fragments retain growth hormone activity or have an antigenic determinant in common with the INSP101 polypeptides.

As used herein, the term "fragment" refers to a polypeptide having an amino acid sequence that is the same as part, but not all, of the amino acid sequence of the INSP101 polypeptides or one of its functional equivalents. The fragments should comprise at least n consecutive amino acids from the sequence and, depending on the particular sequence, n preferably is 7 or more (for example, 8, 10, 12, 14, 16, 18, 20 or more). Small fragments may form an antigenic determinant.

Fragments of the full length INSP101 polypeptides may consist of combinations of 2 or 3 of neighbouring exon sequences in the INSP101 polypeptide sequences, respectively. For example, such combinations include exons 1 and 2, 2 and 3 or 1, 2 and 3. Such fragments are included in the present invention.

Such fragments may be "free-standing", i.e. not part of or fused to other amino acids or polypeptides, or they may be comprised within a larger polypeptide of which they form a part or region. When comprised within a larger polypeptide, the fragment of the invention most preferably forms a single continuous region. For instance, certain preferred embodiments relate to a fragment having a pre- and/or pro-polypeptide region fused to the amino terminus of the fragment and/or an additional region fused to the carboxyl terminus of the fragment. However, several fragments may be comprised within a single larger polypeptide.

The polypeptides of the present invention or their immunogenic fragments (comprising at least one antigenic determinant) can be used to generate ligands, such as polyclonal or monoclonal antibodies, that are immunospecific for the polypeptides. Such antibodies may be employed to isolate or to identify clones expressing the polypeptides of the invention or to purify the polypeptides by affinity chromatography. The antibodies may also be employed as diagnostic or therapeutic aids, amongst other applications, as will be apparent to the skilled reader.

The term "immunospecific" means that the antibodies have substantially greater affinity for the polypeptides of the invention than their affinity for other related polypeptides in the prior art. As used herein, the term "antibody" refers to intact molecules as well as to fragments thereof, such as Fab, F(ab')2 and Fv, which are capable of binding to the antigenic determinant in question. Such antibodies thus bind to the polypeptides of the first aspect of the invention.

By "substantially greater affinity" we mean that there is a measurable increase in the affinity for a polypeptide of the invention as compared with the affinity for known human growth hormones.

Preferably, the affinity is at least 1.5-fold, 2-fold, 5-fold 10-fold, 100-fold, $10^3$-fold, $10^4$-fold, $10^5$-fold, $10^6$-fold or greater for a polypeptide of the invention than for known secreted proteins such as growth hormones.

If polyclonal antibodies are desired, a selected mammal, such as a mouse, rabbit, goat or horse, may be immunised with a polypeptide of the first aspect of the invention. The polypeptide used to immunise the animal can be derived by recombinant DNA technology or can be synthesized chemically. If desired, the polypeptide can be conjugated to a carrier protein. Commonly used carriers to which the polypeptides may be chemically coupled include bovine serum albumin, thyroglobulin and keyhole limpet haemocyanin. The coupled polypeptide is then used to immunise the animal. Serum from the immunised animal is collected and treated according to known procedures, for example by immunoaffinity chromatography.

Monoclonal antibodies to the polypeptides of the first aspect of the invention can also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72 (1983); Cole et al., 77-96 in Monoclonal Antibodies and Cancer Therapy, Alan R. Liss, Inc. (1985).

Panels of monoclonal antibodies produced against the polypeptides of the first aspect of the invention can be screened for various properties, i.e., for isotype, epitope, affinity, etc. Monoclonal antibodies are particularly useful in purification of the individual polypeptides against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et al., Nature, 321, 522 (1986); Verhoeyen et al., Science, 239, 1534 (1988); Kabat et al., J. Immunol., 147, 1709 (1991); Queen et al., Proc. Natl. Acad. Sci. USA, 86, 10029 (1989); Gorman et al., Proc. Natl. Acad. Sci. USA, 88, 34181 (1991); and Hodgson et al., Bio/Technology, 9, 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is an antibody having two different antigen binding domains, each domain being directed against a different epitope.

Phage display technology may be utilised to select genes which encode antibodies with binding activities towards the polypeptides of the invention either from repertoires of PCR amplified V-genes of lymphocytes from humans screened for possessing the relevant antibodies, or from naive libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Preferred nucleic acid molecules of the second and third aspects of the invention are those which encode a polypeptide sequence as recited in SEQ ID NO:2, SEQ ID NO:4, SEQ ID NO: 6, SEQ ID NO:8, or SEQ ID NO:10, and functionally equivalent polypeptides. These nucleic acid molecules may be used in the methods and applications described herein. The nucleic acid molecules of the invention preferably comprise at least n consecutive nucleotides from the sequences disclosed herein where, depending on the particular sequence, n is 10 or more (for example, 12, 14, 15, 18, 20, 25, 30, 35, 40 or more).

The nucleic acid molecules of the invention also include sequences that are complementary to nucleic acid molecules described above (for example, for antisense or probing purposes).

Nucleic acid molecules of the present invention may be in the form of RNA, such as mRNA, or in the form of DNA, including, for instance cDNA, synthetic DNA or genomic DNA. Such nucleic acid molecules may be obtained by cloning, by chemical synthetic techniques or by a combination thereof. The nucleic acid molecules can be prepared, for example, by chemical synthesis using techniques such as solid phase phosphoramidite chemical synthesis, from genomic or cDNA libraries or by separation from an organism. RNA molecules may generally be generated by the in vitro or in vivo transcription of DNA sequences.

The nucleic acid molecules may be double-stranded or single-stranded. Single-stranded DNA may be the coding strand, also known as the sense strand, or it may be the non-coding strand, also referred to as the anti-sense strand.

The term "nucleic acid molecule" also includes analogues of DNA and RNA, such as those containing modified backbones, and peptide nucleic acids (PNA). The term "PNA", as used herein, refers to an antisense molecule or an anti-gene agent which comprises an oligonucleotide of at least five nucleotides in length linked to a peptide backbone of amino acid residues, which preferably ends in lysine. The terminal lysine confers solubility to the composition. PNAs may be pegylated to extend their lifespan in a cell, where they preferentially bind complementary single stranded DNA and RNA and stop transcript elongation (Nielsen, P. E. et al. (1993) Anticancer Drug Des. 8:53-63).

A nucleic acid molecule which encodes a polypeptide of this invention may be identical to the coding sequence of one or more of the nucleic acid molecules disclosed herein.

These molecules also may have a different sequence which, as a result of the degeneracy of the genetic code, encode a polypeptide of SEQ ID NO:2, SEQ ID NO:4, SEQ ID NO: 6, SEQ ID NO:8 or SEQ ID NO:10.

Such nucleic acid molecules may include, but are not limited to, the coding sequence for the mature polypeptide by itself; the coding sequence for the mature polypeptide and additional coding sequences, such as those encoding a leader or secretory sequence, such as a pro-, pre- or prepro-polypeptide sequence; the coding sequence of the mature polypeptide, with or without the aforementioned additional coding sequences, together with further additional, non-coding sequences, including non-coding 5' and 3' sequences, such as the transcribed, non-translated sequences that play a role in transcription (including termination signals), ribosome binding and mRNA stability. The nucleic acid molecules may also include additional sequences which encode additional amino acids, such as those which provide additional functionalities.

The nucleic acid molecules of the second and third aspects of the invention may also encode the fragments or the functional equivalents of the polypeptides and fragments of the first aspect of the invention. Such a nucleic acid molecule may be a naturally-occurring variant such as a naturally-occurring allelic variant, or the molecule may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned nucleic acid molecules by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

The nucleic acid molecules of the invention can also be engineered, using methods generally known in the art, for a variety of reasons, including modifying the cloning, processing, and/or expression of the gene product (the polypeptide). DNA shuffling by random fragmentation and PCR reassembly of gene fragments and synthetic oligonucleotides are included as techniques which may be used to engineer the nucleotide sequences. Site-directed mutagenesis may be used to insert new restriction sites, alter glycosylation patterns, change codon preference, produce splice variants, introduce mutations and so forth.

Nucleic acid molecules which encode a polypeptide of the first aspect of the invention may be ligated to a heterologous sequence so that the combined nucleic acid molecule encodes a fusion protein. Such combined nucleic acid molecules are included within the second or third aspects of the invention. For example, to screen peptide libraries for inhibitors of the activity of the polypeptide, it may be useful to express, using such a combined nucleic acid molecule, a fusion protein that can be recognised by a commercially-available antibody. A fusion protein may also be engineered to contain a cleavage site located between the sequence of the polypeptide of the invention and the sequence of a heterologous protein so that the polypeptide may be cleaved and purified away from the heterologous protein.

The nucleic acid molecules of the invention also include antisense molecules that are partially complementary to nucleic acid molecules encoding polypeptides of the present invention and that therefore hybridize to the encoding nucleic acid molecules (hybridization). Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10, 435 (1989), Okano, J. Neurochem. 56, 560 (1991); O'Connor, J. Neurochem 56, 560 (1991); Lee et al., Nucleic Acids Res 6, 3073 (1979); Cooney et al., Science 241, 456 (1988); Dervan et al., Science 251, 1360 (1991).

The term "hybridization" as used herein refers to the association of two nucleic acid molecules with one another by hydrogen bonding. Typically, one molecule will be fixed to a solid support and the other will be free in solution. Then, the two molecules may be placed in contact with one another under conditions that favour hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al. [supra]).

The inhibition of hybridization of a completely complementary molecule to a target molecule may be examined using a hybridization assay, as known in the art (see, for example, Sambrook et al [supra]). A substantially homologous molecule will then compete for and inhibit the binding of a completely homologous molecule to the target molecule under various conditions of stringency, as taught in Wahl, G. M. and S. L. Berger (1987; Methods Enzymol. 152:399-407) and Kimmel, A. R. (1987; Methods Enzymol. 152:507-511).

"Stringency" refers to conditions in a hybridization reaction that favour the association of very similar molecules over association of molecules that differ. High stringency hybridisation conditions are defined as overnight incubation at 42° C. in a solution comprising 50% formamide, 5×SSC (150 mM NaCl, 15 mM trisodium citrate), 50 mM sodium phosphate (pH7.6), 5× Denhardts solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C. (see Sambrook et al. [supra]). Preferably, the conditions used for hybridization are those of high stringency.

Preferred embodiments of this aspect of the invention are nucleic acid molecules that are at least 90% identical over their entire length to a nucleic acid molecule encoding the INSP101 nucleic acid molecules that are substantially complementary to such nucleic acid molecules.

Preferably, a nucleic acid molecule according to this aspect of the invention comprises a region that is at least 92% identical over its entire length to such coding sequences, or is a nucleic acid molecule that is complementary thereto. In this regard, nucleic acid molecules at least 95%, preferably at least 98% or 99% identical over their entire length to the same are particularly preferred. Preferred embodiments in this respect are nucleic acid molecules that encode polypeptides which retain substantially the same biological function or activity as the INSP101 polypeptides.

The invention also provides a process for detecting a nucleic acid molecule of the invention, comprising the steps of: (a) contacting a nucleic probe according to the invention with a biological sample under hybridizing conditions to form duplexes; and (b) detecting any such duplexes that are formed.

As discussed additionally below in connection with assays that may be utilised according to the invention, a nucleic acid molecule as described above may be used as a hybridization probe for RNA, cDNA or genomic DNA, in order to isolate fill-length cDNAs and genomic clones encoding the INSP101 polypeptides and to isolate cDNA and genomic clones of homologous or orthologous genes that have a high sequence similarity to the gene encoding this polypeptide.

In this regard, the following techniques, among others known in the art, may be utilised and are discussed below for purposes of illusion. Methods for DNA sequencing and analysis are well known and are generally available in the art and may, indeed, be used to practice many of the embodiments of the invention discussed herein. Such methods may employ such enzymes as the Klenow fragment of DNA polymerase I, Sequenase (US Biochemical Corp, Cleveland, Ohio), Taq polymerase (Perkin Elmer), thermostable T7 polymerase (Amersham, Chicago, Ill.), or combinations of polymerases and proof-reading exonucleases such as those found in the ELONGASE Amplification System marketed by Gibco/BRL (Gaithersburg, Md.). Preferably, the sequencing process may be automated using machines such as the Hamilton Micro Lab 2200 (Hamilton, Reno, Nev.), the Peltier Thermal Cycler (PTC200; MJ Research, Watertown, Mass.) and the ABI Catalyst and 373 and 377 DNA Sequencers (Perkin Elmer).

One method for isolating a nucleic acid molecule encoding a polypeptide with an equivalent function to that of the INSP101 polypeptides is to probe a genomic or cDNA library with a natural or artificially-designed probe using standard procedures that are recognised in the art (see, for example, "Current Protocols in Molecular Biology", Ausubel et al. (eds). Greene Publishing Association and John Wiley Interscience, New York, 1989, 1992). Probes comprising at least 15, preferably at least 30, and more preferably at least 50, contiguous bases that correspond to, or are complementary to, nucleic acid sequences from the appropriate encoding gene (SEQ ID NO:1, SEQ ID NO:3, SEQ ID NO:5, SEQ ID NO:7 or SEQ ID NO:9) are particularly useful probes. Such probes may be labelled with an analytically-detectable reagent to facilitate their identification. Useful reagents include, but are not limited to, radioisotopes, fluorescent dyes and enzymes that are capable of catalysing the formation of a detectable product. Using these probes, the ordinarily skilled artisan will be capable of isolating complementary copies of genomic DNA, cDNA or RNA polynucleotides encoding proteins of interest from human, mammalian or other animal sources and screening such sources for related sequences, for example, for additional members of the family, type and/or subtype.

In many cases, isolated cDNA sequences will be incomplete, in that the region encoding the polypeptide will be cut short, normally at the 5' end. Several methods are available to obtain fill length cDNAs, or to extend short cDNAs. Such sequences may be extended utilising a partial nucleotide sequence and employing various methods known in the art to detect upstream sequences such as promoters and regulatory elements. For example, one method which may be employed is based on the method of Rapid Amplification of cDNA Ends (RACE; see, for example, Frohman et al., PNAS USA 85, 8998-9002, 1988). Recent modifications of this technique, exemplified by the Marathon™ technology (Clontech Laboratories Inc.), for example, have significantly simplified the search for longer cDNAs. A slightly different technique, termed "restriction-site" PCR, uses universal primers to retrieve unknown nucleic acid sequence adjacent a known locus (Sarkar, G. (1993) PCR Methods Applic. 2:318-322). Inverse PCR may also be used to amplify or to extend sequences using divergent primers based on a known region (Triglia, T. et al. (1988) Nucleic Acids Res. 16:8186). Another method which may be used is capture PCR which involves PCR amplification of DNA fragments adjacent a known sequence in human and yeast artificial chromosome DNA (Lagerstrom, M. et al. (1991) PCR Methods Applic., 1, 111-119). Another method which may be used to retrieve unknown sequences is that of Parker, J. D. et al. (1991); Nucleic Acids Res. 19:3055-3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

In one embodiment of the invention, the nucleic acid molecules of the present invention may be used for chromosome localisation. In this technique, a nucleic acid molecule is specifically targeted to, and can hybridize with, a particular location on an individual human chromosome. The mapping of relevant sequences to chromosomes according to the present invention is an important step in the confirmatory correlation of those sequences with the gene-associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationships between genes and diseases that have been mapped to the same chromosomal region are then identified through linkage analysis (coinheritance of physically adjacent genes). This provides valuable information to investigators searching for disease genes using positional cloning or other gene discovery techniques. Once the disease or syndrome has been crudely localised by genetic linkage to a particular genomic region, any sequences mapping to that area may represent associated or regulatory genes for further investigation. The nucleic acid molecule may also be used to detect differences in the chromosomal location due to translocation, inversion, etc. among normal, carrier, or affected individuals.

The nucleic acid molecules of the present invention are also valuable for tissue localisation. Such techniques allow the determination of expression patterns of the polypeptide in tissues by detection of the mRNAs that encode them. These techniques include in situ hybridization techniques and nucleotide amplification techniques, such as PCR. Results from these studies provide an indication of the normal functions of the polypeptide in the organism. In addition, comparative studies of the normal expression pattern of mRNAs with that of mRNAs encoded by a mutant gene provide valuable insights into the role of mutant polypeptides in disease. Such inappropriate expression may be of a temporal, spatial or quantitative nature.

Gene silencing approaches may also be undertaken to down-regulate endogenous expression of a gene encoding a polypeptide of the invention. RNA interference (RNAi) (Elbashir, SM et al., Nature 2001, 411, 494-498) is one method of sequence specific post-transcriptional gene silencing that may be employed. Short dsRNA oligonucleotides are synthesised in vitro and introduced into a cell. The sequence specific binding of these dsRNA oligonucleotides triggers the degradation of target mRNA, reducing or ablating target protein expression.

Efficacy of the gene silencing approaches assessed above may be assessed through the measurement of polypeptide expression (for example, by Western blotting), and at the RNA level using TaqMan-based methodologies.

The vectors of the present invention comprise nucleic acid molecules of the invention and may be cloning or expression vectors. The host cells of the invention, which may be transformed, transfected or transduced with the vectors of the invention may be prokaryotic or eukaryotic.

The polypeptides of the invention may be prepared in recombinant form by expression of their encoding nucleic acid molecules in vectors contained within a host cell. Such expression methods are well known to those of skill in the art and many are described in detail by Sambrook et al (supra) and Fernandez & Hoeffler (1998, eds. "Gene expression systems. Using nature for the art of expression". Academic Press, San Diego, London, Boston, New York, Sydney, Tokyo, Toronto).

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et al., (supra). Generally, the encoding gene can be placed under the control of a control element such as a promoter, ribosome binding site (for bacterial expression) and, optionally, an operator, so that the DNA sequence encoding the desired polypeptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviruses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the polypeptides of the invention.

Introduction of nucleic acid molecules encoding a polypeptide of the present invention into host cells can be effected by methods described in many standard laboratory manuals, such as Davis et al., Basic Methods in Molecular Biology (1986) and Sambrook et al., (supra). Particularly suitable methods include calcium phosphate transfection, DEAE-dextran mediated transfection, transvection, microinjection, cationic lipid-mediated transfection, electroporation, transduction, scrape loading, ballistic introduction or infection (see Sambrook et al., 1989 [supra]; Ausubel et al., 1991 [supra]; Spector, Goldman & Leinwald, 1998). In eukaryotic cells, expression systems may either be transient (for example, episomal) or permanent (chromosomal integration) according to the needs of the system.

The encoding nucleic acid molecule may or may not include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the polypeptide or they may be heterologous signals. Leader sequences can be removed by the bacterial host in post-translational processing.

In addition to control sequences, it may be desirable to add regulatory sequences that allow for regulation of the expression of the polypeptide relative to the growth of the host cell. Examples of regulatory sequences are those which cause the expression of a gene to be increased or decreased in response to a chemical or physical stimulus, including the presence of a regulatory compound or to various temperature or metabolic conditions. Regulatory sequences are those non-translated regions of the vector, such as enhancers, promoters and 5' and 3' untranslated regions. These interact with host cellular proteins to carry out transcription and translation. Such regulatory sequences may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the Bluescript phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (for example, heat shock, RUBISCO and storage protein genes) or from plant viruses (for example, viral promoters or leader sequences) may be cloned into the vector. In mammalian cell systems, promoters from mammalian genes or from mammalian viruses are preferable. If it is necessary to generate a cell line that contains multiple copies of the sequence, vectors based on SV40 or EBV may be used with an appropriate selectable marker.

An expression vector is constructed so that the particular nucleic acid coding sequence is located in the vector with the appropriate regulatory sequences, the positioning and orientation of the coding sequence with respect to the regulatory sequences being such that the coding sequence is transcribed under the "control" of the regulatory sequences, i.e., RNA polymerase which binds to the DNA molecule at the control sequences transcribes the coding sequence. In some cases it may be necessary to modify the sequence so that it may be attached to the control sequences with the appropriate orientation; i.e., to maintain the reading frame.

The control sequences and other regulatory sequences may be ligated to the nucleic acid coding sequence prior to insertion into a vector. Alternatively, the coding sequence can be cloned directly into an expression vector that already contains the control sequences and an appropriate restriction site.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines.

In the baculovirus system, the materials for baculovirus/insect cell expression systems are commercially available in kit form from, inter alia, Invitrogen, San Diego Calif. (the "MaxBac" kit). These techniques are generally known to those skilled in the art and are described fully in Summers and Smith, Texas Agricultural Experiment Station Bulletin No. 1555 (1987). Particularly suitable host cells for use in this system include insect cells such as *Drosophila* S2 and *Spodoptera* Sf9 cells.

There are many plant cell culture and whole plant genetic expression systems known in the art. Examples of suitable plant cellular genetic expression systems include those described in U.S. Pat. Nos. 5,693,506 5,659,122; and 5,608,143. Additional examples of genetic expression in plant cell culture has been described by Zenk, Phytochemistry 30, 3861-3863 (1991).

In particular, all plants from which protoplasts can be isolated and cultured to give whole regenerated plants can be utilised, so that whole plants are recovered which contain the transferred gene. Practically all plants can be regenerated from cultured cells or tissues, including but not limited to all major species of sugar cane, sugar beet, cotton, fruit and other trees, legumes and vegetables.

Examples of particularly preferred bacterial host cells include *streptococci, staphylococci, E. coli, Streptomyces* and *Bacillus subtilis* cells.

Examples of particularly suitable host cells for fungal expression include yeast cells (for example, *S. cerevisiae*) and *Aspergillus* cells.

Any number of selection systems are known in the art that may be used to recover transformed cell lines. Examples include the herpes simplex virus thymidine kinase (Wigler, M. et al. (1977) Cell 11:223-32) and adenine phosphoribosyltransferase (Lowy, I. et al. (1980) Cell 22:817-23) genes that can be employed in tk$^-$ or aprt$^±$ cells, respectively.

Also, antimetabolite, antibiotic or herbicide resistance can be used as the basis for selection; for example, dihydrofolate reductase (DHFR) that confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinotricin acetyltransferase, respectively. Additional selectable genes have been described, examples of which will be clear to those of skill in the art.

Although the presence or absence of marker gene expression suggests that the gene of interest is also present, its presence and expression may need to be confirmed. For example, if the relevant sequence is inserted within a marker gene sequence, transformed cells containing the appropriate sequences can be identified by the absence of marker gene function. Alternatively, a marker gene can be placed in tandem with a sequence encoding a polypeptide of the invention under the control of a single promoter. Expression of the marker gene in response to induction or selection usually indicates expression of the tandem gene as well.

Alternatively, host cells that contain a nucleic acid sequence encoding a polypeptide of the invention and which express said polypeptide may be identified by a variety of procedures known to those of skill in the art. These procedures include, but are not limited to, DNA-DNA or DNA-RNA hybridizations and protein bioassays, for example, fluorescence activated cell sorting (FACS) or immunoassay techniques (such as the enzyme-linked immunosorbent assay [ELISA] and radioimmunoassay [RIA]), that include membrane, solution, or chip based technologies for the detection and/or quantification of nucleic acid or protein (see Hampton, R. et al. (1990) Serological Methods, a Laboratory Manual, APS Press, St Paul, Minn.) and Maddox, D. E. et al. (1983) J. Exp. Med, 158, 1211-1216).

A wide variety of labels and conjugation techniques are known by those skilled in the art and may be used in various nucleic acid and amino acid assays. Means for producing labelled hybridization or PCR probes for detecting sequences related to nucleic acid molecules encoding polypeptides of the present invention include oligolabelling, nick translation, end-labelling or PCR amplification using a labelled polynucleotide. Alternatively, the sequences encoding the polypeptide of the invention may be cloned into a vector for the production of an mRNA probe. Such vectors are known in the art, are commercially available, and may be used to synthesise RNA probes in vitro by addition of an appropriate RNA polymerase such as T7, T3 or SP6 and labelled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)).

Suitable reporter molecules or labels, which may be used for ease of detection, include radionuclides, enzymes and fluorescent, chemiluminescent or chromogenic agents as well as substrates, cofactors, inhibitors, magnetic particles, and the like.

Nucleic acid molecules according to the present invention may also be used to create transgenic animals, particularly rodent animals. Such transgenic animals form a further aspect of the present invention. This may be done locally by modification of somatic cells, or by germ line therapy to incorporate heritable modifications. Such transgenic animals may be particularly useful in the generation of animal models for drug molecules effective as modulators of the polypeptides of the present invention.

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography is particularly useful for purification. Well known techniques for refolding proteins may be employed to regenerate an active conformation when the polypeptide is denatured during isolation and or purification.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptides such as histidine-tryptophan modules that allow purification on immobilised metals, protein A domains that allow purification on immobilised immunoglobulin, and the domain utilised in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the polypeptide of the invention may be used to facilitate purification. One such expression vector provides for expression of a fusion protein containing the polypeptide of the invention fused to several histidine residues preceding a thioredoxin or an enterokinase cleavage site. The histidine residues facilitate purification by IMAC (immobilised metal ion affinity chromatography as described in Porath, J. et al. (1992), Prot. Exp. Purif. 3:263-281) while the thioredoxin or enterokinase cleavage site provides a means for purifying the polypeptide from the fusion protein. A discussion of vectors which contain fusion proteins is provided in Kroll, D. J. et al. (1993; DNA Cell Biol. 12:441-453).

If the polypeptide is to be expressed for use in screening assays, generally it is preferred that it be produced at the surface of the host cell in which it is expressed. In this event, the host cells may be harvested prior to use in the screening assay, for example using techniques such as fluorescence activated cell sorting (FACS) or immunoaffinity techniques.

If the polypeptide is secreted into the medium, the medium can be recovered in order to recover and purify the expressed polypeptide. If polypeptide is produced intracellularly, the cells must first be lysed before the polypeptide is recovered.

The polypeptide of the invention can be used to screen libraries of compounds in any of a variety of drug screening techniques. Such compounds may activate (agonise) or inhibit (antagonise) the level of expression of the gene or the activity of the polypeptide of the invention and form a further aspect of the present invention. Preferred compounds are effective to alter the expression of a natural gene which encodes a polypeptide of the first aspect of the invention or to regulate the activity of a polypeptide of the first aspect of the invention.

Agonist or antagonist compounds may be isolated from, for example, cells, cell-free preparations, chemical libraries or natural product mixtures. These agonists or antagonists may be natural or modified substrates, ligands, enzymes, receptors or structural or functional mimetics. For a suitable review of such screening techniques, see Coligan et al., Current Protocols in Immunology 1 (2):Chapter 5 (1991).

Compounds that are most likely to be good antagonists are molecules that bind to the polypeptide of the invention without inducing the biological effects of the polypeptide upon binding to it. Potential antagonists include small organic molecules, peptides, polypeptides and antibodies that bind to the polypeptide of the invention and thereby inhibit or extinguish its activity. In this fashion, binding of the polypeptide to normal cellular binding molecules may be inhibited, such that the normal biological activity of the polypeptide is prevented.

The polypeptide of the invention that is employed in such a screening technique may be free in solution, affixed to a solid support, borne on a cell surface or located intracellularly. In general, such screening procedures may involve using appropriate cells or cell membranes that express the polypeptide that are contacted with a test compound to observe binding, or stimulation or inhibition of a functional response. The functional response of the cells contacted with the test compound is then compared with control cells that were not contacted with the test compound. Such an assay may assess whether the test compound results in a signal generated by activation of the polypeptide, using an appropriate detection system. Inhibitors of activation are generally assayed in the presence of a known agonist and the effect on activation by the agonist in the presence of the test compound is observed.

A preferred method for identifying an agonist or antagonist compound of a polypeptide of the present invention comprises:

(a) contacting a cell expressing on the surface thereof the polypeptide according to the first aspect of the invention, the polypeptide being associated with a second component capable of providing a detectable signal in response to the binding of a compound to the polypeptide, with a compound to be screened under conditions to permit binding to the polypeptide; and (b) determining whether the compound binds to and activates or inhibits the polypeptide by measuring the level of a signal generated from the interaction of the compound with the polypeptide.

A further preferred method for identifying an agonist or antagonist of a polypeptide of the invention comprises:

(a) contacting a cell expressing on the surface thereof the polypeptide, the polypeptide being associated with a second component capable of providing a detectable signal in response to the binding of a compound to the polypeptide, with a compound to be screened under conditions to permit binding to the polypeptide; and (b) determining whether the compound binds to and activates or inhibits the polypeptide by comparing the level of a signal generated from the interaction of the compound with the polypeptide with the level of a signal in the absence of the compound.

In further preferred embodiments, the general methods that are described above may further comprise conducting the identification of agonist or antagonist in the presence of labelled or unlabelled ligand for the polypeptide.

In another embodiment of the method for identifying agonist or antagonist of a polypeptide of the present invention comprises:

determining the inhibition of binding of a ligand to cells which have a polypeptide of the invention on the surface thereof, or to cell membranes containing such a polypeptide, in the presence of a candidate compound under conditions to permit binding to the polypeptide, and determining the amount of ligand bound to the polypeptide. A compound capable of causing reduction of binding of a ligand is considered to be an agonist or antagonist. Preferably the ligand is labelled.

More particularly, a method of screening for a polypeptide antagonist or agonist compound comprises the steps of:

(a) incubating a labelled ligand with a whole cell expressing a polypeptide according to the invention on the cell surface, or a cell membrane containing a polypeptide of the invention, (b) measuring the amount of labelled ligand bound to the whole cell or the cell membrane;

(c) adding a candidate compound to a mixture of labelled ligand and the whole cell or the cell membrane of step (a) and allowing the mixture to attain equilibrium;

(d) measuring the amount of labelled ligand bound to the whole cell or the cell membrane after step (c); and (e) comparing the difference in the labelled ligand bound in step (b) and (d), such that the compound which causes the reduction in binding in step (d) is considered to be an agonist or antagonist.

The INSP101 polypeptides of the present invention may modulate a variety of physiological and pathological processes, including processes such as cellular proliferation and migration within the immune system. Thus, the biological activity of the INSP101 polypeptides can be examined in systems that allow the study of such modulatory activities, using a variety of suitable assays.

For example, for observing cell growth inhibition, one can use a solid or liquid medium. In a solid medium, cells undergoing growth inhibition can easily be selected from the subject cell group by comparing the sizes of colonies formed. In a liquid medium, growth inhibition can be screened by measuring culture medium turbity or incorporation of labelled thymidine in DNA. Typically, the incorporation of a nucleoside analog into newly synthesised DNA may be employed to measure proliferation (i.e., active cell growth) in a population of cells. For example, bromodeoxyuridine (BrdU) can be employed as a DNA labelling reagent and anti-BrdU mouse monoclonal antibodies can be employed as a detection reagent. This antibody binds only to cells containing DNA which has incorporated bromodeoxyuridine. A number of detection methods may be used in conjunction with this assay including immunofluorescence, immunohistochemical, ELISA, and colorimetric methods. Kits that include bromodeoxyuridine (BrdU) and anti-BrdU mouse monoclonal antibody are commercially available from Boehringer Mannheim (Indianapolis, Ind.).

The INSP101 polypeptides may be found to modulate a variety of physiological and pathological processes in a dose-dependent manner in the above-described assays. Thus, the "functional equivalents" of the INSP101 polypeptides include polypeptides that exhibit any of the same modulatory activities in the above-described assays in a dose-dependent manner. Although the degree of dose-dependent activity need not be identical to that of the INSP101 polypeptides, preferably the "functional equivalents" will exhibit substantially similar dose-dependence in a given activity assay compared to the INSP101 polypeptides.

In certain of the embodiments described above, simple binding assays may be used, in which the adherence of a test compound to a surface bearing the polypeptide is detected by means of a label directly or indirectly associated with the test compound or in an assay involving competition with a labelled competitor. In another embodiment, competitive drug screening assays may be used, in which neutralising antibodies that are capable of binding the polypeptide specifically compete with a test compound for binding. In this manner, the antibodies can be used to detect the presence of any test compound that possesses specific binding affinity for the polypeptide.

Assays may also be designed to detect the effect of added test compounds on the production of mRNA encoding the polypeptide in cells. For example, an ELISA may be constructed that measures secreted or cell-associated levels of polypeptide using monoclonal or polyclonal antibodies by standard methods known in the art, and this can be used to search for compounds that may inhibit or enhance the production of the polypeptide from suitably manipulated cells or tissues. The formation of binding complexes between the polypeptide and the compound being tested may then be measured.

Another technique for drug screening which may be used provides for high throughput screening of compounds having suitable binding affinity to the polypeptide of interest (see International patent application WO84/03564). In this method, large numbers of different small test compounds are synthesised on a solid substrate, which may then be reacted with the polypeptide of the invention and washed. One way of immobilising the polypeptide is to use non-neutralising antibodies. Bound polypeptide may then be detected using methods that are well known in the art. Purified polypeptide can also be coated directly onto plates for use in the aforementioned drug screening techniques.

The polypeptide of the invention may be used to identify membrane-bound or soluble receptors, through standard receptor binding techniques that are known in the art, such as ligand binding and crosslinking assays in which the polypeptide is labelled with a radioactive isotope, is chemically modified, or is fused to a peptide sequence that facilitates its detection or purification, and incubated with a source of the putative receptor (for example, a composition of cells, cell membranes, cell supernatants, tissue extracts, or bodily fluids). The efficacy of binding may be measured using biophysical techniques such as surface plasmon resonance and spectroscopy. Binding assays may be used for the purification and cloning of the receptor, but may also identify agonists and antagonists of the polypeptide, that compete with the binding of the polypeptide to its receptor. Standard methods for conducting screening assays are well understood in the art.

The INSP101 polypeptides of the present invention may modulate a variety of physiological and pathological processes, including processes such as the secretion of hormones, cellular growth and cellular metastasis, including cancer cell metastasis (Torosian, M. H. & Donoway, R. B., 1991, Cancer, 67 (9):2280-2283). Thus, the biological activity of the INSP101 polypeptides can be examined in systems that allow the study of such modulatory activities, using a variety of suitable assays.

For example, for observing the effect of the INSP101 polypeptides of the present invention on cellular metastasis, one can employ one or more of the methods described in Ohtaki et al., Nature. 2001 May 31;411 (6837):613-7 or the publications referred to therein.

For example, for observing the effect of the INSP101 polypeptides of the present invention on the secretion of hormones, one can employ one or more of the methods described in Hinuma et al., Nature. 1998 May 21;393 (6682): 272-6 or Hinuma et al, Nat Cell Biol. 2000 October;2 (10): 703-8 or the publications referred to therein.

The INSP101 polypeptides of the present invention may also be used for the identification and characterisation of receptors, particularly growth hormone receptors, which interact with the INSP101 polypeptides of the present invention. Suitable methods of identification and characterisation include, but are not limited to, those described in Hinuma et al., Nat Cell Biol. 2000 October;2 (10):703-8 and the International patent application published as WO01/17958 or the publications referred to therein.

The INSP101 polypeptides may be found to modulate a variety of physiological and pathological processes in a dose-dependent manner in the above-described assays. Thus, the "functional equivalents" of the INSP101 polypeptides include polypeptides that exhibit any of the same modulatory activities in the above-described assays in a dose-dependent manner. Although the degree of dose-dependent activity need not be identical to that of the INSP101 polypeptides, preferably the "functional equivalents" will exhibit substantially similar dose-dependence in a given activity assay compared to the INSP101 polypeptides.

The invention also includes a screening kit useful in the methods for identifying agonists, antagonists, ligands, receptors, substrates, enzymes, that are described above.

The invention includes the agonists, antagonists, ligands, receptors, substrates and enzymes, and other compounds which modulate the activity or antigenicity of the polypeptide of the invention discovered by the methods that are described above.

The invention also provides pharmaceutical compositions comprising a polypeptide, nucleic acid, ligand or compound of the invention in combination with a suitable pharmaceutical carrier. These compositions may be suitable as therapeutic or diagnostic reagents, as vaccines, or as other immunogenic compositions, as outlined in detail below.

According to the terminology used herein, a composition containing a polypeptide, nucleic acid, ligand or compound [X] is "substantially free of" impurities [herein, Y] when at least 85% by weight of the total X+Y in the composition is X. Preferably, X comprises at least about 90% by weight of the total of X+Y in the composition, more preferably at least about 95%, 98% or even 99% by weight.

The pharmaceutical compositions should preferably comprise a therapeutically effective amount of the polypeptide, nucleic acid molecule, ligand, or compound of the invention. The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs. The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.01 mg/kg to 50 mg/kg, preferably 0.05 mg/kg to 10 mg/kg. Compositions may be administered individually to a patient or may be administered in combination with other agents, drugs or hormones.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The pharmaceutical compositions utilised in this invention may be administered by any number of routes including, but not limited to, oral, intravenous, intramuscular, intraarterial, intramedullary, intrathecal, intraventricular, transdermal or transcutaneous applications (for example, see WO98/20734), subcutaneous, intraperitoneal, intranasal, enteral, topical, sublingual, intravaginal or rectal means. Gene guns or hyposprays may also be used to administer the pharmaceutical compositions of the invention. Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

If the activity of the polypeptide of the invention is in excess in a particular disease state, several approaches are available. One approach comprises administering to a subject an inhibitor compound (antagonist) as described above, along with a pharmaceutically acceptable carrier in an amount effective to inhibit the function of the polypeptide, such as by blocking the binding of ligands, substrates, enzymes, receptors, or by inhibiting a second signal, and thereby alleviating the abnormal condition. Preferably, such antagonists are antibodies. Most preferably, such antibodies are chimeric and/or humanised to minimise their immunogenicity, as described previously.

In another approach, soluble forms of the polypeptide that retain binding affinity for the ligand, substrate, enzyme, receptor, in question, may be administered. Typically, the polypeptide may be administered in the form of fragments that retain the relevant portions.

In an alternative approach, expression of the gene encoding the polypeptide can be inhibited using expression blocking techniques, such as the use of antisense nucleic acid molecules (as described above), either internally generated or separately administered. Modifications of gene expression can be obtained by designing complementary sequences or antisense molecules (DNA, RNA, or PNA) to the control, 5' or regulatory regions (signal sequence, promoters, enhancers and introns) of the gene encoding the polypeptide. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes. Such oligonucleotides may be administered or may be generated in situ from expression in vivo.

In addition, expression of the polypeptide of the invention may be prevented by using ribozymes specific to its encoding mRNA sequence. Ribozymes are catalytically active RNAs that can be natural or synthetic (see for example Usman, N, et al., Curr. Opin. Struct. Biol (1996) 6 (4), 527-33). Synthetic ribozymes can be designed to specifically cleave mRNAs at selected positions thereby preventing translation of the mRNAs into functional polypeptide. Ribozymes may be synthesised with a natural ribose phosphate backbone and natural bases, as normally found in RNA molecules. Alternatively the ribozymes may be synthesised with non-natural backbones, for example, 2'-O-methyl RNA, to provide protection from ribonuclease degradation and may contain modified bases.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine and butosine, as well as acetyl-, methyl-, thio- and similarly modified forms of adenine, cytidine, guanine, thymine and uridine which are not as easily recognised by endogenous endonucleases.

For treating abnormal conditions related to an under-expression of the polypeptide of the invention and its activity, several approaches are also available. One approach comprises administering to a subject a therapeutically effective amount of a compound that activates the polypeptide, i.e., an agonist as described above, to alleviate the abnormal condition. Alternatively, a therapeutic amount of the polypeptide in combination with a suitable pharmaceutical carrier may be administered to restore the relevant physiological balance of polypeptide.

Gene therapy may be employed to effect the endogenous production of the polypeptide by the relevant cells in the subject. Gene therapy is used to treat permanently the inappropriate production of the polypeptide by replacing a defective gene with a corrected therapeutic gene.

Gene therapy of the present invention can occur in vivo or ex vivo. Ex vivo gene therapy requires the isolation and purification of patient cells, the introduction of a therapeutic gene and introduction of the genetically altered cells back into the patient. In contrast, in vivo gene therapy does not require isolation and purification of a patient's cells.

The therapeutic gene is typically "packaged" for administration to a patient. Gene delivery vehicles may be non-viral, such as liposomes, or replication-deficient viruses, such as adenovirus as described by Berkner, K. L., in Curr. Top. Microbiol. Immunol., 158, 39-66 (1992) or adeno-associated virus (AAV) vectors as described by Muzyczka, N., in Curr. Top. Microbiol. Immunol., 158, 97-129 (1992) and U.S. Pat. No. 5,252,479. For example, a nucleic acid molecule encoding a polypeptide of the invention may be engineered for expression in a replication-defective retroviral vector. This expression construct may then be isolated and introduced into a packaging cell transduced with a retroviral plasmid vector containing RNA encoding the polypeptide, such that the packaging cell now produces infectious viral particles containing the gene of interest. These producer cells may be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the administration of "naked DNA" in which the therapeutic gene is directly injected into the bloodstream or muscle tissue.

In situations in which the polypeptides or nucleic acid molecules of the invention are disease-causing agents, the invention provides that they can be used in vaccines to raise antibodies against the disease causing agent.

Vaccines according to the invention may either be prophylactic (ie. to prevent infection) or therapeutic (ie. to treat disease after infection). Such vaccines comprise immunising antigen(s), immunogen(s), polypeptide(s), protein(s) or nucleic acid, usually in combination with pharmaceutically-acceptable carriers as described above, which include any carrier that does not itself induce the production of antibodies harmful to the individual receiving the composition. Additionally, these carriers may function as immunostimulating agents ("adjuvants"). Furthermore, the antigen or immunogen may be conjugated to a bacterial toxoid, such as a toxoid from diphtheria, tetanus, cholera, H. pylori, and other pathogens.

Since polypeptides may be broken down in the stomach, vaccines comprising polypeptides are preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient, and aqueous and non-aqueous sterile suspensions which may include suspending agents or thickening agents.

The vaccine formulations of the invention may be presented in unit-dose or multi-dose containers. For example, sealed ampoules and vials and may be stored in a freeze-dried condition requiring only the addition of the sterile liquid carrier immediately prior to use. The dosage will depend on the specific activity of the vaccine and can be readily determined by routine experimentation.

Genetic delivery of antibodies that bind to polypeptides according to the invention may also be effected, for example, as described in International patent application WO98/55607.

The technology referred to as jet injection (see, for example, www.powderject.com) may also be useful in the formulation of vaccine compositions.

A number of suitable methods for vaccination and vaccine delivery systems are described in International patent application WO00/29428.

This invention also relates to the use of nucleic acid molecules according to the present invention as diagnostic reagents. Detection of a mutated form of the gene characterised by the nucleic acid molecules of the invention which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acid molecules for diagnosis may be obtained from a subject's cells, such as from blood, urine, saliva, tissue biopsy or autopsy material. The genomic DNA may be used directly for detection or may be amplified enzymatically by using PCR, ligase chain reaction (LCR), strand displacement amplification (SDA), or other amplification techniques (see Saiki et al., Nature, 324, 163-166 (1986); Bej, et al., Crit. Rev. Biochem. Molec. Biol., 26, 301-334 (1991); Birkenmeyer et al., J. Virol. Meth., 35, 117-126 (1991); Van Brunt, J., Bio/Technology, 8, 291-294 (1990)) prior to analysis.

In one embodiment, this aspect of the invention provides a method of diagnosing a disease in a patient, comprising assessing the level of expression of a natural gene encoding a polypeptide according to the invention and comparing said level of expression to a control level, wherein a level that is different to said control level is indicative of disease. The method may comprise the steps of:

a) contacting a sample of tissue from the patient with a nucleic acid probe under stringent conditions that allow the formation of a hybrid complex between a nucleic acid molecule of the invention and the probe;

b) contacting a control sample with said probe under the same conditions used in step a);

c) and detecting the presence of hybrid complexes in said samples;

wherein detection of levels of the hybrid complex in the patient sample that differ from levels of the hybrid complex in the control sample is indicative of disease.

A further aspect of the invention comprises a diagnostic method comprising the steps of:

a) obtaining a tissue sample from a patient being tested for disease;

b) isolating a nucleic acid molecule according to the invention from said tissue sample; and c) diagnosing the patient for disease by detecting the presence of a mutation in the nucleic acid molecule which is associated with disease.

To aid the detection of nucleic acid molecules in the above-described methods, an amplification step, for example using PCR, may be included.

Deletions and insertions can be detected by a change in the size of the amplified product in comparison to the normal genotype. Point mutations can be identified by hybridizing amplified DNA to labelled RNA of the invention or alternatively, labelled antisense DNA sequences of the invention. Perfectly-matched sequences can be distinguished from mismatched duplexes by RNase digestion or by assessing differences in melting temperatures. The presence or absence of the mutation in the patient may be detected by contacting DNA with a nucleic acid probe that hybridises to the DNA under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation in the corresponding portion of the DNA strand.

Such diagnostics are particularly useful for prenatal and even neonatal testing.

Point mutations and other sequence differences between the reference gene and "mutant" genes can be identified by other well-known techniques, such as direct DNA sequencing or single-strand conformational polymorphism, (see Orita et al., Genomics, 5, 874-879 (1989)). For example, a sequencing primer may be used with double-stranded PCR product or a single-stranded template molecule generated by a modified PCR. The sequence determination is performed by conventional procedures with radiolabelled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, for example, through the use of allele-specific oligonucleotides for PCR amplification of sequences that differ by single nucleotides.

DNA sequence differences may also be detected by alterations in the electrophoretic mobility of DNA fragments in gels, with or without denaturing agents, or by direct DNA sequencing (for example, Myers et al., Science (1985) 230: 1242). Sequence changes at specific locations may also be revealed by nuclease protection assays, such as RNase and S1 protection or the chemical cleavage method (see Cotton et al., Proc. Natl. Acad. Sci. USA (1985) 85: 4397-4401).

In addition to conventional gel electrophoresis and DNA sequencing, mutations such as microdeletions, aneuploidies, translocations, inversions, can also be detected by in situ analysis (see, for example, Keller et al., DNA Probes, 2nd Ed., Stockton Press, New York, N.Y., USA (1993)), that is, DNA or RNA sequences in cells can be analysed for mutations without need for their isolation and/or immobilisation onto a membrane. Fluorescence in situ hybridization (FISH) is presently the most commonly applied method and numerous reviews of FISH have appeared (see, for example, Trachuck et al., Science, 250, 559-562 (1990), and Trask et al., Trends, Genet., 7, 149-154 (1991)).

In another embodiment of the invention, an array of oligonucleotide probes comprising a nucleic acid molecule according to the invention can be constructed to conduct efficient screening of genetic variants, mutations and polymorphisms. Array technology methods are well known and have general applicability and can be used to address a variety of questions in molecular genetics including gene expression, genetic linkage, and genetic variability (see for example: M. Chee et al., Science (1996), Vol 274, pp 610-613).

In one embodiment, the array is prepared and used according to the methods described in PCT application WO95/11995 (Chee et al); Lockhart, D. J. et al. (1996) Nat. Biotech. 14: 1675-1680); and Schena, M. et al. (1996) Proc. Natl. Acad. Sci. 93: 10614-10619). Oligonucleotide pairs may range from two to over one million. The oligomers are synthesized at designated areas on a substrate using a light-directed chemical process. The substrate may be paper, nylon or other type of membrane, filter, chip, glass slide or any other suitable solid support. In another aspect, an oligonucleotide may be synthesized on the surface of the substrate by using a chemical coupling procedure and an ink jet application apparatus, as described in PCT application WO95/251116 (Baldeschweiler et al). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and over one million which lends itself to the efficient use of commercially-available instrumentation.

In addition to the methods discussed above, diseases may be diagnosed by methods comprising determining, from a sample derived from a subject, an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods.

Assay techniques that can be used to determine levels of a polypeptide of the present invention in a sample derived from a host are well-known to those of skill in the art and are discussed in some detail above (including radioimmunoassays, competitive-binding assays, Western Blot analysis and ELISA assays). This aspect of the invention provides a diagnostic method which comprises the steps of: (a) contacting a ligand as described above with a biological sample under conditions suitable for the formation of a ligand-polypeptide complex; and (b) detecting said complex.

Protocols such as ELISA, RIA, and FACS for measuring polypeptide levels may additionally provide a basis for diagnosing altered or abnormal levels of polypeptide expression. Normal or standard values for polypeptide expression are established by combining body fluids or cell extracts taken from normal mammalian subjects, preferably humans, with antibody to the polypeptide under conditions suitable for complex formation. The amount of standard complex formation may be quantified by various methods, such as by photometric means.

Antibodies which specifically bind to a polypeptide of the invention may be used for the diagnosis of conditions or diseases characterised by expression of the polypeptide, or in assays to monitor patients being treated with the polypeptides, nucleic acid molecules, ligands and other compounds of the invention. Antibodies useful for diagnostic purposes may be prepared in the same manner as those described above for therapeutics. Diagnostic assays for the polypeptide include methods that utilise the antibody and a label to detect the polypeptide in human body fluids or extracts of cells or tissues. The antibodies may be used with or without modification, and may be labelled by joining them, either covalently or non-covalently, with a reporter molecule. A wide variety of reporter molecules known in the art may be used, several of which are described above.

Quantities of polypeptide expressed in subject, control and disease samples from biopsied tissues are compared with the standard values. Deviation between standard and subject values establishes the parameters for diagnosing disease. Diagnostic assays may be used to distinguish between absence, presence, and excess expression of polypeptide and to monitor regulation of polypeptide levels during therapeutic intervention. Such assays may also be used to evaluate the efficacy of a particular therapeutic treatment regimen in animal studies, in clinical trials or in monitoring the treatment of an individual patient.

A diagnostic kit of the present invention may comprise:
(a) a nucleic acid molecule of the present invention;
(b) a polypeptide of the present invention; or
(c) a ligand of the present invention.

In one aspect of the invention, a diagnostic kit may comprise a first container containing a nucleic acid probe that hybridises under stringent conditions with a nucleic acid molecule according to the invention; a second container containing primers useful for amplifying the nucleic acid molecule; and instructions for using the probe and primers for facilitating the diagnosis of disease. The kit may further comprise a third container holding an agent for digesting unhybridised RNA.

In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or disorder or susceptibility to disease or disorder in which endocrine proteins are implicated. Such diseases and disorders may include reproductive disorders, preganancy disorder, such as gestational trophoblastic disease, developmental disorders such as Silver-Russell syndrome, growth disorders, growth hormone deficiency, Cushing's disease, endocrine disorders, cell proliferative disorders, including neoplasm, carcinoma, pituitary tumour, ovary tumour, melanoma, lung, colorectal, breast, pancreas, head and neck, placental site trophoblastic tumor, adenocarcinoma, choriocarcinoma, osteosarcoma and other solid tumours; angiogeneisis, myeloproliferative disorders; autoimmune/inflammatory disorders; cardiovascular disorders; neurological disorders, pain; metabolic disorders including diabetes mellitus, osteoporosis, and obesity, cachexia, AIDS, renal disease; lung injury; ageing; infections including viral infection, bacterial infection, fungal infection and parasitic infection, and other pathological conditions. Preferably, the disease is one in which endocrine function, particularly growth hormones are implicated.

Various aspects and embodiments of the present invention will now be described in more detail by way of example, with particular reference to the INSP101 polypeptide.

It will be appreciated that modification of detail may be made without departing from the scope of the invention.

BRIEF DESCRIPTION OF THE FIGURES

FIG. 1 shows an alignment of full length INSP101 (SEQ ID NO:6) versus P01241, Pituitary growth hormone (GH-N) from *H. sapiens*. The A-B loop is marked by asterisks.

FIG. 2 compares the splicing pattern of P01241, pituitary growth hormone (GH-N) from *H. sapiens* with the splicing pattern of the novel splice variant INSP101.

FIG. 3: Predicted nucleotide sequence of INSP101 with translation. Underlined sequence denotes the predicted signal sequence.

FIG. 4: Map of plasmid pCRII-TOPO-E00974

FIG. 5: Alignment of INSP101 with plasmid #13686

FIG. 6: Nucleotide sequence and translation of cloned INSP101 product

FIG. 7: Map of pENTR-INSP101-6HIS

FIG. 8: Map of pEAK12d-INSP101-6HIS

EXAMPLES

Example 1

INSP101 was identified as containing five exons. FIG. 2 compares the splicing pattern of P01241, pituitary growth hormone (GH-N) from *H. sapiens* with the splicing pattern of the novel splice variant INSP101. The INSP101 exon 2nov polypeptide and the INSP101 exon 3nov polypeptide are alternative exons produced by alternative splicing; the splice variant has an extended exon2 (2nov) and a truncated exon3 (3nov) in comparison to the wild type protein.

The diagram also displays the main secondary structure elements of pituitary growth hormone (GH-N). GH-N is composed of four alpha helices (A, B, C and D), and of particular importance is the "A-B loop" which connects helix A to helix B. The A-B loop is a critical component of the GH-N interaction surface which binds the Growth Hormone receptor (Wells J A, PNAS vol. 93, pp. 1-6 1996 Binding in the growth hormone receptor complex). It is evident that the novel splice variant INSP101 has new residues inserted in the A-B loop (due to the extension of exon2). Similarly, the truncation of exon3 will lead to the removal of some GH-N residues in the A-B loop. Thus INSP101 differs from GH-N principally in the composition of the A-B loop, and since this loop is a primary determinant in binding to the growth hormone receptor, INSP101 is predicted to exhibit altered receptor binding properties (in terms of binding affinity and/or receptor selectivity).

These experimental predictions will be confirmed subsequently by a directed experimental test. For example, a number of different assays may be used to determine the effects of human Growth Hormones on binding (see, for example, Well J. A. PNAS Vol. 93 pp. 1-6, 1996), including the use of monoclonal antibodies to precipitate 1:1 complexes of growth hormone and receptor, and the hGH-induced dimerization of hGHbp molecules in solution by the quenching of a fluorescent tag placed near the C terminus of the hGHbp (see Well J. A. PNAS Vol. 93 pp. 1-6, 1996). [hGHbp=extracellular domain of GH receptor]

Example 2

Cloning of INSP101

1.1 Preparation of Human Pituitary cDNA

First strand cDNA was prepared from human pituitary total RNA (Clontech) using Superscript II RNase H⁻ Reverse Transcriptase (Invitrogen) according to the manufacturer's protocol. 1 µl Oligo (dT)$_{15}$ primer (500 µg/ml, Promega), 2 µg human lung total RNA, 1 µl of 10 mM dNTP mix (10 mM each of dATP, dGTP, dCTP and dTTP at neutral pH) and sterile distilled water to a final volume of 12 µl were combined in a 1.5 ml eppendorf tube, heated to 65° C. for 5 min and then chilled on ice. The contents were collected by brief centrifugation and 4 µl of 5× First-Strand Buffer, 2 µl of 0.1 M DTT, and 1 μl of RNaseOUT Recombinant Ribonuclease Inhibitor (40 units/μl, Invitrogen) were added. The contents of the tube were mixed gently and incubated at 42° C. for 2 min, then 1 μl (200 units) of SuperScript II enzyme was added and mixed gently by pipetting. The mixture was incubated at 42° C. for 50 min and then inactivated by heating at 70° C. for 15 min. To remove RNA complementary to the cDNA, 1 μl (2 units) of E. coli RNase H (Invitrogen) was added and the reaction mixture incubated at 37° C. for 20 min. The final 21 μl reaction mix was diluted by adding 179 μl sterile water to give a total volume of 200 μl.

1.2 Gene Specific Cloning Primers for PCR

A pair of PCR primers having a length of between 18 and 25 bases were designed for amplifying the complete coding sequence of the virtual cDNA using Primer Designer Software (Scientific & Educational Software, PO Box 72045, Durham, N.C. 27722-2045, USA). PCR primers were optimized to have a Tm close to 55±10° C. and a GC content of 40-60%. Primers were selected which had high selectivity for the target sequence (INSP101) with little or no non-specific priming.

1.3 PCR Amplification of INSP101 from Human Pituitary cDNA

Gene-specific cloning primers (INSP101-CP1 and INSP101-CP2, (Table 1) were designed to amplify a cDNA fragment covering the entire coding sequence of the INSP101 prediction. The gene-specific cloning primers INSP101-CP1 and INSP101-CP2 were used with human pituitary cDNA as the template. The PCR was performed in a final volume of 50 μl containing 1× AmpliTaq™ buffer, 200 μM dNTPs, INSP101-CP1, 50 pmoles of INSP101-CP2, 2.5 units of AmpliTaq™ (Perkin Elmer) and 100 ng of lung cDNA using an MJ Research DNA Engine, programmed as follows: 94° C., 2 min; 40 cycles of 94° C., 1 min, 50° C., 1 min, and 72° C., 1 min; followed by 1 cycle at 72° C. for 7 min and a holding cycle at 4° C. PCR products were purified directly using the Wizard PCR Preps DNA Purification System (Promega).

1.4 Subcloning of PCR Products

PCR products were subcloned into the topoisomerase I modified cloning vector (pCRII TOPO) using the TA cloning kit purchased from the Invitrogen Corporation using the conditions specified by the manufacturer. Briefly, 4 μl of gel purified PCR product from the human library pool P amplification was incubated for 15 min at room temperature with 1 μl of TOPO vector and 1 μl salt solution. The reaction mixture was then transformed into E. coli strain TOP10 (Invitrogen) as follows: a 50 μl aliquot of One Shot TOP10 cells was thawed on ice and 2 μl of TOPO reaction was added. The mixture was incubated for 15 min on ice and then heat shocked by incubation at 42° C. for exactly 30 s. Samples were returned to ice and 250 μl of warm SOC media (room temperature) was added. Samples were incubated with shaking (220 rpm) for 1 h at 37° C. The transformation mixture was then plated on L-broth (LB) plates containing ampicillin (100 μg/ml) and incubated overnight at 37° C.

1.5 Colony PCR

Colonies were inoculated into 50 μl sterile water using a sterile toothpick. A 10 μl aliquot of the inoculum was then subjected to PCR in a total reaction volume of 20 μl containing 1× AmpliTaq™ buffer, 200 μM dNTPs, 20 pmoles T7 primer, 20 pmoles of SP6 primer, 1 unit of AmpliTaq™ (Perkin Elmer) using an MJ Research DNA Engine. The cycling conditions were as follows: 94° C., 2 min; 30 cycles of 94° C., 30 sec. 47° C., 30 sec and 72° C. for 1 min. Samples were then maintained at 4° C. (holding cycle) before further analysis.

PCR reaction products were analyzed on 1% agarose gels in 1×TAE buffer. One colony which gave the expected PCR product size (+187 bp due to the multiple cloning site or MCS) was grown up overnight at 37° C. in 5 ml L-Broth (LB) containing ampicillin (100 μg/ml), with shaking at 220 rpm.

1.6 Plasmid DNA Preparation and Sequencing

Miniprep plasmid DNA was prepared from the 5 ml culture using a Qiaprep Turbo 9600 robotic system (Qiagen) or Wizard Plus SV Minipreps kit (Promega cat. no. 1460) according to the manufacturer's instructions. Plasmid DNA was eluted in 100 μl of sterile water. The DNA concentration was measured using an Eppendorf BO photometer. Plasmid DNA (200-500 ng) was subjected to DNA sequencing with the T7 primer and SP6 primer using the BigDyeTerminator system (Applied Biosystems cat. no. 4390246) according to the manufacturer's instructions. The primer sequences are shown in Table 1. Sequencing reactions were purified using Dye-Ex columns (Qiagen) or Montage SEQ 96 cleanup plates (Millipore cat. no. LSKS09624) then analyzed on an Applied Biosystems 3700 sequencer. Sequence analysis revealed that the cloned sequence in plasmid pCRII-TOPO was identical to GenBank E00974 (plasmid 13686) (FIG. 4).

1.7 PCR Amplification of 5' and 3' End of INSP101 from Plasmid13686

PCR primers were designed to amplify 5' and 3' end of INSP101 individually (table 1). The forward primer for 5' end of INSP101 (INSP101-B1P-5'-F) also contains the partial sequence of the Gateway attB1 site (5' GCAGGCTTC) and a Kozak sequence (5' GCCACC). The reverse primer for 5' end of INSP101 (INSP101-5'-R) has a 25 base overlap with the forward primer for the 3' end of INSP101. The forward primer for 3' end of INSP101 (INSP101-3'-F) has a 26 bp overlap with the reverse primer for the 5' end. The reverse primer for 3' end of INSP101 (INSP101-3'-R) contains a 5 HIS sequence (FIG. 5).

For amplification of INSP101 5' end, the PCR reaction was performed in a final volume of 50 μl and contained 0.5 μl of plasmid 13686 miniprep DNA, 2 μl of 5 mM dNTPs (Amersham Pharmacia Biotech), 6 μl of INSP101-B1p-5'-F (10 μM), 6 μl of INSP101-5'R, 5 μl of 10×Pfu buffer and 0.5 μl of Pfu polymerase (3 U/μl) (# M774B, Promega). The PCR conditions were 94° C. for 2 min; 30 cycles of 94° C. for 30 s, 55° C. for 30 s and 72° C. for 1 min, and a holding cycle of 4° C. Reaction products were loaded onto a 1.5% agarose gel (1×TAE) and PCR products of the correct size (211 bp) were gel-purified using a Qiaquick Gel Extraction Kit (Qiagen cat. no. 28704) and eluted in 50 μl of elution buffer (Qiagen).

INSP101 3' end was amplified using the same reaction conditions as above but with primers INSP101-3'-F and INSP101-3'-R, 5 μl of 10× AmpliTaq buffer and 0.5 μl of AmpliTaq DNA Polymerase (Applied Biosystems, # N808-0155, 5 U/ul). PCR products of 441 bp were gel purified as above.

2. Assembly of the 5' and 3' Ends of INSP101 to Generate INSP101 ORF

5' and 3' end of INSP 101 were assembled in a PCR reaction containing 5 μl of gel purified 5' end, 2 μl of gel purified 3' end, 2 μl of 5 mM dNTPs, 6 μl of INSP101-B1P-5'-F (10 μM), 6 μl of INSP101-3'-R (10 μM), 5 μl of 10×Pfu buffer, 0.5 μl Pfu polymerase (3 U/μl; Promega cat. no. M774B). The reaction conditions were: 94° C., 4 min; 10 cycles of 94° C. for 30 s, 48° C. for 30 s and 70° C. for 2 min; 25 cycles of 94° C. for 30 s, 52° C., for 30 s and 70° C. for 2 min; an additional elongation step of 70° C. for 10 min; and a holding cycle at 4° C. Reaction products were analysed on a 1.5% agarose gel (1×TAE). PCR products of the predicted size (627 bp) were gel purified using a Qiaquick Gel Extraction Kit (Qiagen cat. no. 28704) and eluted in 50 μl of elution buffer (Qiagen). The resultant product (INSP101 ORF) contains the ORF of the INSP101 flanked at the 5' end by an attB1 site and Kozak sequence, and at the 3' end by a 5HIS tag encoding sequence (FIG. 6).

3. Subcloning of the INSP101 ORF into pDONR221

The INSP101 ORF was subcloned into pDONR221 using the Gateway™ cloning system (Invitrogen). A partial attB1 recombination site was added to the 5' end of INSP101 ORF and a 6HIS tag sequence, stop codon and attB2 recombination site was added to the 3' end of the INSP101 ORF in a 50 µl PCR reaction containing 2 µl of gel purified INSP101 ORF PCR product, 2 µl of 5 mM dNTPs (Amersham Pharmacia Biotech), 3 µl of GCP-Forward (10 µM), 3 µl of GCP-Reverse (10 µM), 5 µl of 10× AmpliTaq buffer and 0.5 µl of AmpliTaq DNA Polymerase (Applied Biosystems, # N808-0155, 5 U/ul) in a final volume of 50 µl. The PCR conditions were 94° C. for 2 min; 30 cycles of 94° C. for 30 s; 55° C. for 30 s and 72° C. for 1 min; an additional elongation step of 72° C. for 3 min and a holding cycle of 4° C. Reaction products were analysed on a 1.5% agarose gel (1×TAE) and PCR products of the correct size (685 bp) were gel purified using a Qiaquick Gel Extraction Kit (Qiagen cat. no. 28704) and eluted in 50 µl of elution buffer (Qiagen). The purified PCR product (Gateway-modified INSP101 ORF) was then transferred to pDONR221 using BP clonase as follows: 1.5 µl of Gateway-modified INSP101 ORF was incubated with 0.5 µl pDONR221 (0.1 µg/µl), 1 µl BP buffer and 1 µl of BP clonase enzyme mix (Invitrogen) in a final volume of 5 µl at RT for 2 h. The reaction was stopped by addition of 0.5 µl proteinase K (2 µg/µl) and incubated at 37° C. for a further 10 min. An aliquot of this reaction (3 µl) was used to transform 50 µl *E. coli* DH5alpha cell (Invitrogen) by heat shock. The transformation mix was incubated in a 0.2 ml PCR tube on ice for 30 min and then transferred into a 42° C. water bath for 45 s. The tubes were returned to ice for 2 min, and the transformation mix transferred to a 12 ml polypropylene tube. Samples were then diluted by addition of 900 µl of SOC medium and incubated for 1 h at 37° C. with shaking. Transformants (200 µl) were plated on LB plates containing 40 µg/µl kanamycin and incubated for 72 h at RT. Plasmid mini prep DNA was isolated from 8 resultant colonies using a Qiaprep Turbo 9600 robotic system (Qiagen) and subjected to DNA sequencing with M13F and M13R sequencing primers using the BigDyeTerminator system (Applied Biosystems cat. no. 4390246) according to the manufacturer's instructions. Sequencing reactions were purified using Dye-Ex columns (Qiagen) or Montage SEQ 96 cleanup plates (Millipore cat. no. LSKS09624) then analyzed on an Applied Biosystems 3700 sequencer.

3. Mutagenesis of pDONR221-INSP101

The sequencing verification showed that all of the pDONR-221-INSP101 clones had a stop codon between ORF and the 6HIS tag. Site-directed mutagenesis was used to delete the stop codon. A Stratagene Quik Change XL Site-Directed Mutagenesis kit (cat. # 200517) and primers INSP101-mut-F and INSP101-mut-R were used according to the manufacturer's instructions. Plasmid mini prep DNA was isolated from 8 of the resultant colonies using a Qiaprep Turbo 9600 robotic system (Qiagen) and subjected to DNA sequencing with M13F and M13R sequencing primers using the BigDyeTerminator system (Applied Biosystems cat. no. 4390246) according to the manufacturer's instructions. Sequencing reactions were purified using Dye-Ex columns (Qiagen) or Montage SEQ 96 cleanup plates (Millipore cat. no. LSKS09624) then analyzed on an Applied Biosystems 3700 sequencer.

4. Subcloning of the INSP101 ORF to Expression Vector pEAK12d

Plasmid eluate (1.5 µl) from a pDONR221 clone containing the correct sequence of the INSP101 ORF (pENTR-INSP101-6HIS, plasmid ID 14577) (FIG. 7) was then used in a recombination reaction containing 1.5 µl pEAK12d (0.1 µg/µl), 2 µl LR buffer and 1.5 µl of LR clonase (Invitrogen) in a final volume of 10 µl. The mixture was incubated at RT for 1 h, stopped by addition of 1 µl proteinase K (2 µg/µl) and incubated at 37° C. for a further 10 min. An aliquot of this reaction (1 µl) was used to transform 20 µl of *E. coli* DH10B cells (Invitrogen) (diluted 1/5 in sterile water) by electroporation using a Biorad Gene Pulser according to the manufacturer's recommendations. Electroporated cells were transferred to 12 ml polypropylene tubes, diluted by addition of 1 ml of SOC medium and incubated for 1 h at 37° C. Transformants were plated on LB-ampicillin plates and incubated overnight at 37° C. Mini prep DNA was prepared from 3 colonies using a Qiaprep Turbo 9600 robotic system (Qiagen) and eluted in 50 µl of elution buffer. 0.5 µl of each miniprep was then subjected to PCR in a total reaction volume of 50 µl containing 2 µl of 5 mM dNTPs, 3 µl of 10 µM pEAK12-F, 3 µl of 10 µM pEAK12-R, 5 µl of 10× AmpliTaq™ buffer and 0.5 µl AmpliTaq™ (Applied Biosystems cat. no. N808-0155). The cycling conditions were as follows: 94° C. for 2 min; 30 cycles of 94° C. for 30 s, 55° C. for 30 s, and 72° C. for 1 min; 1 cycle, 72° C. for 3 min. Samples were then maintained at 4° C. (holding cycle) before further analysis.

PCR reaction products were analyzed on 1% agarose gels in 1×TAE buffer. One colony which gave the expected PCR product size (1010 bp) was used to prepare CsCl gradient purified maxi-prep DNA of plasmid pEAK12d-INSP101-6HIS (plasmid ID 14578) (FIG. 6) from a 500 ml culture (Sambrook J. et al., in Molecular Cloning, a Laboratory Manual, 2$^{nd}$ edition, 1989, Cold Spring Harbor Laboratory Press). The resultant plasmid DNA was resuspended at a concentration of 1 µg/µl in TE buffer and sequence verified with pEAK12d F and pEAK12d R primers as described above.

TABLE 1

Primers for INSP101 cloning and sequencing

| Primer | Sequence (5'-3') |
|---|---|
| GCP Forward | G GGG ACA AGT TTG TAC AAA AAA GCA GGC TTC <u>GCC ACC</u> (SEQ ID NO: 11) |
| GCP Reverse | GGG GAC CAC TTT GTA CAA GAA AGC TGG GTT TCA *ATG GTG ATG GTG ATG GTG* (SEQ ID NO: 12) |
| INSP101-B1P-5'-F | GCA GGC TTC GCC ACC ATG GCT ACA GGC TCC CGG ACG TCC C (SEQ ID NO: 13) |

TABLE 1-continued

Primers for INSP101 cloning and sequencing

| Primer | Sequence (5'-3') |
|---|---|
| INSP101-5'-R | TAG ACT CCA TTC CCC AAG AGC TTA CAA ACT CCT GGT AGG TGT CAA AGG CC (SEQ ID NO: 14) |
| INSP101-3'-F | AGG AGT TTG TAA GCT CTT GGG GAA TGG AGT CTA TTC CGA TGT CAA AGG CC (SEQ ID NO: 15) |
| INSP101-3'-R | *GTG ATG GTG ATG GTG* CTA GAA GCC ACA GCT GCC CTC CAC (SEQ ID NO: 16) |
| INSP101-mut-F | GGG CAG CTG TGG CTT CCA CCA TCA CCA TCA CCA TTG (SEQ ID NO: 17) |
| INSP101-mut-R | AAT GGT GAT GGT GAT GGT GGA AGC CAC AGC TGC CCT C (SEQ ID NO: 18) |
| pEAK12-F | GCC AGC TTG GCA CTT GAT GT (SEQ ID NO: 19) |
| pEAK12-R | GAT GGA GGT GGA CGT GTC AG (SEQ ID NO: 20) |
| M13F | CAG GAA ACA GCT ATG ACC (SEQ ID NO: 21) |
| M13R | TGT AAA ACG ACG GCC AGT (SEQ ID NO: 22) |
| INSP101-CP1 | GCT GCA ATG GCT ACA GGC TCC C (SEQ ID NO: 23) |
| INSP101-CP2 | AGA GCA CAC AGC TGC CCT CC (SEQ ID NO: 24) |

Underlined sequence = Kozak sequence
Bold = Stop codon
*Italic* sequence = His tag
Shaded sequence = overlap with adjacent cDNA part

Example 3

Expression and Purification of INSP101

Further experiments may now be performed to determine the tissue distribution and expression levels of the INSP101 polypeptides in vivo, on the basis of the nucleotide and amino acid sequence disclosed herein.

The presence of the transcripts for INSP101 may be investigated by PCR of cDNA from different human tissues. The INSP101 transcripts may be present at very low levels in the samples tested. Therefore, extreme care is needed in the design of experiments to establish the presence of a transcript in various human tissues as a small amount of genomic contamination in the RNA preparation will provide a false positive result. Thus, all RNA should be treated with DNAse prior to use for reverse transcription. In addition, for each tissue a control reaction may be set up in which reverse transcription was not undertaken (a −ve RT control).

For example, 1 μg of total RNA from each tissue may be used to generate cDNA using Multiscript reverse transcriptase (ABI) and random hexamer primers. For each tissue, a control reaction is set up in which all the constituents are added except the reverse transcriptase (−ve RT control). PCR reactions are set up for each tissue on the reverse transcribed RNA samples and the minus RT controls. INSP101-specific primers may readily be designed on the basis of the sequence information provided herein. The presence of a product of the correct molecular weight in the reverse transcribed sample together with the absence of a product in the minus RT control may be taken as evidence for the presence of a transcript in that tissue. Any suitable cDNA libraries may be used to screen for the INSP101 transcripts, not only those generated as described above.

The tissue distribution pattern of the INSP101 polypeptides will provide further useful information in relation to the function of those polypeptides.

In addition, further experiments may now be performed using the pEAK12d-INSP101-6HIS expression vectors. Transfection of mammalian cell lines with these vectors may enable the high level expression of the INSP101 proteins and thus enable the continued investigation of the functional characteristics of the INSP101 polypeptides. The following material and methods are an example of those suitable in such experiments:

Cell Culture

Human Embryonic Kidney 293 cells expressing the Epstein-Barr virus Nuclear Antigen (HEK293-EBNA, Invitrogen) are maintained in suspension in Ex-cell VPRO serum-free medium (seed stock, maintenance medium, JRH). Sixteen to 20 hours prior to transfection (Day-1), cells are seeded in 2× T225 flasks (50 ml per flask in DMEM/F12 (1:1) containing 2% FBS seeding medium (JRH) at a density of $2 \times 10^5$ cells/ml). The next day (transfection day 0) transfection takes place using the JetPEI™ reagent (2 μl/μg of plasmid DNA, PolyPlus-transfection). For each flask, plasmid DNA is co-transfected with GFP (fluorescent reporter gene) DNA. The transfection mix is then added to the 2×T225 flasks and incubated at 37° C. (5% $CO_2$) for 6 days. Confirmation of positive transfection may be carried out by qualitative fluorescence examination at day 1 and day 6 (Axiovert 10 Zeiss).

On day 6 (harvest day), supernatants from the two flasks are pooled and centrifuged (e.g. 4° C., 400 g) and placed into a pot bearing a unique identifier. One aliquot (500 µl) is kept for QC of the 6His-tagged protein (internal bioprocessing QC).

Scale-up batches may be produced by following the protocol called "PEI transfection of suspension cells", referenced BP/PEI/HH/02/04, with PolyEthyleneImine from Polysciences as transfection agent.

Purification Process

The culture medium sample containing the recombinant protein with a C-terminal 6His tag is diluted with cold buffer A (50 mM $NaH_2PO_4$; 600 mM NaCl; 8.7% (w/v) glycerol, pH 7.5). The sample is filtered then through a sterile filter (Millipore) and kept at 4° C. in a sterile square media bottle (Nalgene).

The purification is performed at 4° C. on the VISION workstation (Applied Biosystems) connected to an automatic sample loader (Labomatic). The purification procedure is composed of two sequential steps, metal affinity chromatography on a Poros 20 MC (Applied Biosystems) column charged with Ni ions (4.6×50 mm, 0.83 ml), followed by gel filtration on a Sephadex G-25 medium (Amersham Pharmacia) column (1.0×10 cm).

For the first chromatography step the metal affinity column is regenerated with 30 column volumes of EDTA solution (100 mM EDTA; 1 M NaCl; pH 8.0), recharged with Ni ions through washing with 15 column volumes of a 100 mM $NiSO_4$ solution, washed with 10 column volumes of buffer A, followed by 7 column volumes of buffer B (50 mM $NaH_2PO_4$; 600 mM NaCl; 8.7% (w/v) glycerol, 400 mM; imidazole, pH 7.5), and finally equilibrated with 15 column volumes of buffer A containing 15 mM imidazole. The sample is transferred, by the Labomatic sample loader, into a 200 ml sample loop and subsequently charged onto the Ni metal affinity column at a flow rate of 10 ml/min. The column is washed with 12 column volumes of buffer A, followed by 28 column volumes of buffer A containing 20 mM imidazole. During the 20 mM imidazole wash loosely attached contaminating proteins are eluted from the column. The recombinant His-tagged protein is finally eluted with 10 column volumes of buffer B at a flow rate of 2 ml/min, and the eluted protein is collected.

For the second chromatography step, the Sephadex G-25 gel-filtration column is regenerated with 2 ml of buffer D (1.137M NaCl; 2.7 mM KCl; 1.5 mM $KH_2PO_4$; 8 mM $Na_2HPO_4$; pH 7.2), and subsequently equilibrated with 4 column volumes of buffer C (137 mM NaCl; 2.7 mM KCl; 1.5 mM $KH_2PO_4$; 8 mM $Na_2HPO_4$; 20% (w/v) glycerol; pH 7.4). The peak fraction eluted from the Ni-column is automatically loaded onto the Sephadex G-25 column through the integrated sample loader on the VISION and the protein is eluted with buffer C at a flow rate of 2 ml/min. The fraction was filtered through a sterile centrifugation filter (Millipore), frozen and stored at −80° C. An aliquot of the sample is analyzed on SDS-PAGE (4-12% NuPAGE gel; Novex) Western blot with anti-His antibodies. The NuPAGE gel may be stained in a 0.1% Coomassie blue R250 staining solution (30% methanol, 10% acetic acid) at room temperature for 1 h and subsequently destained in 20% methanol, 7.5% acetic acid until the background is clear and the protein bands clearly visible.

Following the electrophoresis the proteins are electrotransferred from the gel to a nitrocellulose membrane. The membrane is blocked with 5% milk powder in buffer E (137 mM NaCl; 2.7 mM KCl; 1.5 mM $KH_2PO_4$; 8 mM $Na_2HPO_4$; 0.1% Tween 20, pH 7.4) for 1 h at room temperature, and subsequently incubated with a mixture of 2 rabbit polyclonal anti-His antibodies (G-18 and H-15, 0.2 µg/ml each; Santa Cruz) in 2.5% milk powder in buffer E overnight at 4° C. After a further 1 hour incubation at room temperature, the membrane is washed with buffer E (3×10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3×10 minutes), the membrane is developed with the ECL kit (Amersham Pharmacia) for 1 min. The membrane is subsequently exposed to a Hyperfilm (Amersham Pharmacia), the film developed and the western blot image visually analysed.

For samples that showed detectable protein bands by Coomassie staining, the protein concentration may be determined using the BCA protein assay kit (Pierce) with bovine serum albumin as standard.

Furthermore, overexpression or knock-down of the expression of the polypeptides in cell lines may be used to determine the effect on transcriptional activation of the host cell genome. Dimerisation partners, co-activators and co-repressors of the INSP101 polypeptide may be identified by immunoprecipitation combined with Western blotting and immunoprecipitation combined with mass spectroscopy.

List of INSP101 Specific Sequences (Note: for Amino Acids Encoded by Exon-Exon Junctions, the Amino Acid will be Assigned to the More 5' Exon.)

```
(INSP101 nucleotide sequence exon 2nov)              SEQ ID NO:1
  1 GGCTCCCGGA CGTCCCTGCT CCTGGCTTTT GGCCTGCTCT GCCTGCCCTG
 51 GCTTCAAGAG GGCAGTGCCT TCCCAACCAT TCCCTTATCC AGGCTTTTTG
101 ACAACGCTAT GCTCCGCGCC CATCGTCTGC ACCAGCTGGC CTTTGACACC
151 TACCAGGAGT TTGTAAGCTC TTGGGGAATG G (INSP101 protein sequence exon 2nov)                 SEQ ID NO:2
  1 GSRTSLLLAF GLLCLPWLQE GSAFPTIPLS RLFDNAMLRA HRLHQLAFDT
 51 YQEFVSSWGM E (INSP101 nucleotide sequence exon 3nov)              SEQ ID NO:3
  1 AGTCTATTCC GAGACCCTCC AACAGGGAGG AAACACAACA GAAATCC (INSP101 protein sequence exon 3nov)                 SEQ ID NO:4
  1 SIPTPSNREE TQQKS (INSP101 contiguous nucleotide sequence exons        SEQ ID NO:5
2nov and 3nov)
  1 GGCTCCCGGA CGTCCCTGCT CCTGGCTTTT GGCCTGCTCT GCCTGCCCTG
 51 GCTTCAAGAG GGCAGTGCCT TCCCAACCAT TCCCTTATCC AGGCTTTTTG
```

-continued
```
101 ACAACGCTAT GCTCCGCGCC CATCGTCTGC ACCAGCTGGC CTTTGACACC
151 TACCAGGAGT TTGTAAGCTC TTGGGGAATG GAGTCTATTC CGACACCCTC
201 CAACAGGGAG GAAACACAAC AGAAATCC
```

(INSP101 contiguous protein sequence exons    SEQ ID NO:6
2nov and 3nov)
```
  1 GSRTSLLLAF GLLCLPWLQE GSAFPTIPLS RLFDNAMLRA KRLHQLAFDT
 51 YQEFVSSWGM ESIPTPSNRE ETQQKS
```

(INSP101 full length nucleotide sequence)    SEQ ID NO:7
```
  1 ATGGCTACAG GCTCCCGGAC GTCCCTGCTC CTGGCTTTTG GCCTGCTCTG
 51 CCTGCCCTGG CTTCAAGAGG GCAGTGCCTT CCCAACCATT CCCTTATCCA
101 GGCTTTTTGA CAACGCTATG CTCCGCGCCC ATCGTCTGCA CCAGCTGGCC
151 TTTGACACCT ACCAGGAGTT TGTAAGCTCT TGGGGAATGG AGTCTATTCC
201 GACACCCTCC AACAGGGAGG AAACACAACA GAAATCCAAC CTAGAGCTGC
251 TCCGCATCTC CCTGCTCTC ATCCAGTCGT GGCTGGAGCC CGTGCAGTTC
301 CTCAGGAGTG TCTTCGCCAA CAGCCTGGTG TACGGCGCCT CTGACAGCAA
351 CGTCTATGAC CTCCTAAAGG ACCTAGAGGA AGGCATCCAA ACGCTGATGG
401 GGAGGCTGGA AGATGGCAGC CCCCGGACTG GCAGATCTT CAAGCAGACC
451 TACAGCAAGT TCGACACAAA CTCACACAAC GATGACGCAC TACTCAAGAA
501 CTACGGGCTG CTCTACTGCT TCAGGAAGGA CATGGACAAG GTCGAGACAT
551 TCCTGCGCAT CGTGCAGTGC CGCTCTGTGG AGGGCAGCTG TGGCTTCTAG
```

(INSP101 full length protein sequence)    SEQ ID NO:8
```
  1 MATGSRTSLL LAFGLLCLPW LQEGSAFPTI PLSRLFDNAM LRAHRLHQLA
 51 FDTYQEFVSS WGMESIPTPS NREETQQKSN LELLRTSLLL IQSWLEPVQF
101 LRSVFANSLV YGASDSNVYD LLKDLEEGIQ TLMGRLEDGS PRTGQIFKQT
151 YSKFDTNSHN DDALLKNYGL LYCFRKDMDK VETFLRIVQC RSVEGSCGF
```

(INSP101 full length nucleotide sequence-without    SEQ ID NO:9
signal peptide region)
```
  1 TTCCCAACCA TTCCCTTATC CAGGCTTTTT GACAACGCTA TGCTCCGCGC
 51 CCATCGTCTG CACCAGCTGG CCTTTGACAC CTACCACGAG TTTGTAAGGT
101 CTTGGGGAAT GGAGTCTATT CCGACACCCT CCAACAGGGA GGAAACACAA
151 CAGAAATCCA ACCTAGAGCT GCTCCGCATC TCCCTGCTGC TCATCCAGTC
201 GTGGCTGGAG CCCGTGCAGT TCCTCAGGAG TGTCTTCGCC AACAGCCTGG
251 TGTACGGCGC CTCTGACAGC AACGTCTATG ACCTCCTAAA GGACCTAGAG
301 GAAGGCATCC AAACGCTGAT GGGGAGGCTG GAAGATGGCA GCCCCCGGAC
351 TGGGCAGATC TTCAAGCAGA CCTACAGCAA GTTCGACACA AACTCACACA
401 ACGATGACGC ACTACTCAAG AACTACGGGC TGCTCTACTG CTTCAGGAAG
451 GACATGGACA AGGTCGAGAC ATTCCTGCGC ATCGTGCAGT GCCGCTCTGT
501 GGAGGGCAGC TGTGGCTTCT AG
```

(INSP101 full length protein sequence-without    SEQ ID NO:10
signal peptide region)
```
  1 FPTIPLSRLF DNAMLRAHRL HQLAFDTYQE FVSSWGMESI PTPSNREETQ
 51 QKSNLELLRI SLLLIQSWLE PVQFLRSVFA NSLVYGASDS NVYDLLKDLE
101 EGIQTLMGRL EDGSPRTGQI FKQTYSKFDT NSHNDDALLK NYGLLYCFRK
151 DMDKVETFLR IVQCRSVEGS CGF
```

---

The invention claimed is:

1. An isolated polypeptide comprising:
   a) SEQ ID NO:8;
   b) SEQ ID NO:10;
   c) a polypeptide that has greater than 98% sequence identity to SEQ ID NO: 8 and has an activity of human growth hormone; or
   d) a polypeptide that has greater than 98% sequence identity to SEQ ID NO: 10 and has an activity of human growth hormone.

2. The isolated polypeptide according to claim 1, wherein said polypeptide comprises SEQ ID NO: 8.

3. The isolated polypeptide according to claim 1, wherein said polypeptide comprises SEQ ID NO: 10.

4. The isolated polypeptide according to claim 1, wherein said polypeptide consists of SEQ ID NO: 8.

5. The isolated polypeptide according to claim 1, wherein said polypeptide consists of SEQ ID NO: 10.

6. The isolated polypeptide according to claim 1, wherein said polypeptide has greater than 98% sequence identity to SEQ ID NO: 8 and has an activity of human growth hormone.

7. The isolated polypeptide according to claim 1, wherein said polypeptide has greater than 98% sequence identity to SEQ ID NO: 10 and has an activity of human growth hormone.

8. A composition comprising a pharmaceutically acceptable carrier and a polypeptide comprising:
   a) SEQ ID NO:8;
   b) SEQ ID NO:10;
   c) a polypeptide that has greater than 98% sequence identity to SEQ ID NO: 8 and has an activity of human growth hormone; or
   d) a polypeptide that has greater than 98% sequence identity to SEQ ID NO: 10 and has an activity of human growth hormone.

9. The composition according to claim 8, wherein said polypeptide comprises SEQ ID NO: 8.

10. The composition according to claim 8, wherein said polypeptide comprises SEQ ID NO: 10.

11. The composition according to claim 8, wherein said polypeptide consists of SEQ ID NO: 8.

12. The composition according to claim 8, wherein said polypeptide consists of SEQ ID NO: 10.

13. The composition according to claim 8, wherein said polypeptide has greater than 98% sequence identity to SEQ ID NO: 8 and has an activity of human growth hormone.

14. The composition according to claim 8, wherein said polypeptide has greater than 98% sequence identity to SEQ ID NO: 10 and has an activity of human growth hormone.

* * * * *

UNITED STATES PATENT AND TRADEMARK OFFICE
CERTIFICATE OF CORRECTION

PATENT NO. : 7,531,508 B2
APPLICATION NO. : 10/537142
DATED : May 12, 2009
INVENTOR(S) : Richard Joseph Fagan et al.

It is certified that error appears in the above-identified patent and that said Letters Patent is hereby corrected as shown below:

Column 2,
Line 48, "August;29 (8):16424)" should read --Aug;29(8):1642-4--.

Column 16,
Line 49, "fill-length" should read --full-length--.
Line 55, "purposes of illusion" should read --purposes of illustration--.

Column 17,
Line 31, "fill length" should read --full length--.

Column 21,
Line 4, "5,693,506 5,659,122; and" should read --5,693,506; 5,659,122; and--.

Columns 39-40,
Line 7, Table 1, "INSP101-3'-F AGG AGT TTG TAA GCT CTT GGG GAA TGG AGT CTA TTC CGA TGT CAA AGG CC (SEQ ID NO: 15)" should read --INSP101-3'-F AGG AGT TTG TAA GCT CTT GGG GAA TGG AGT CTA TTC CGA CAC CCT CCA ACA (SEQ ID NO: 15)--.

Column 42,
Line 60,
SEQ ID NO: 3, "1 AGTCTATTCC GAGACCCTCC AACAGGGAGG AAACACAACA GAAATCC" should read --1 AGTCTATTCC GACACCCTCC AACAGGGAGG AAACACAACA GAAATCC--.

Column 43,
Line 5-6,
SEQ ID NO: 6, "1 GSRTSLLLAF GLLCLPWLQE GSAFPTIPLS RLFDNAMLRA KRLHQLAFDT
    51 YQEFVSSWGM ESIPTPSNRE ETQQKS"
should read    --1 GSRTSLLLAF GLLCLPWLQE GSAFPTIPLS RLFDNAMLRA HRLHQLAFDT
    51 YQEFVSSWGM ESIPTPSNRE ETQQKS--.

CERTIFICATE OF CORRECTION (continued)
U.S. Pat. No. 7,531,508 B2

Line 30,
SEQ ID NO: 9, "51 CCATCGTCTG CACCAGCTGG CCTTTGACAC CTACCACGAG
    TTTGTAAGGT"
should read --51 CCATCGTCTG CACCAGCTGG CCTTTGACAC CTACCAGGAG
    TTTGTAAGCT--.

Signed and Sealed this

Thirteenth Day of April, 2010

David J. Kappos
*Director of the United States Patent and Trademark Office*

SEQUENCE LISTING

<160> NUMBER OF SEQ IDS NOS: 26

<210> SEQ ID NO 1
<211> LENGTH: 181
<212> TYPE: DNA
<213> ORGANISM: Homo sapiens

<400> SEQUENCE: 1

```
ggctcccgga cgtccctgct cctggctttt ggcctgctct gcctgccctg gcttcaagag      60
ggcagtgcct cccaaccat tcccttatcc aggcttttg acaacgctat gctccgcgcc     120
catcgtctgc accagctggc ctttgacacc taccaggagt ttgtaagctc ttggggaatg     180
g                                                                    181
```

<210> SEQ ID NO 2
<211> LENGTH: 61
<212> TYPE: PRT
<213> ORGANISM: Homo sapiens

<400> SEQUENCE: 2

Gly Ser Arg Thr Ser Leu Leu Leu Ala Phe Gly Leu Leu Cys Leu Pro
1               5                   10                  15

Trp Leu Gln Glu Gly Ser Ala Phe Pro Thr Ile Pro Leu Ser Arg Leu
                20                  25                  30

Phe Asp Asn Ala Met Leu Arg Ala His Arg Leu His Gln Leu Ala Phe
            35                  40                  45

Asp Thr Tyr Gln Glu Phe Val Ser Ser Trp Gly Met Glu
        50                  55                  60

<210> SEQ ID NO 3
<211> LENGTH: 47
<212> TYPE: DNA
<213> ORGANISM: Homo sapiens

<400> SEQUENCE: 3
agtctattcc gacaccctcc aacagggagg aaacacaaca gaaatcc           47

<210> SEQ ID NO 4
<211> LENGTH: 15
<212> TYPE: PRT
<213> ORGANISM: Homo sapiens

<400> SEQUENCE: 4

Ser Ile Pro Thr Pro Ser Asn Arg Glu Glu Thr Gln Gln Lys Ser
1               5                   10                  15

<210> SEQ ID NO 5
<211> LENGTH: 228
<212> TYPE: DNA
<213> ORGANISM: Homo sapiens

<400> SEQUENCE: 5
ggctcccgga cgtccctgct cctggctttt ggcctgctct gcctgccctg gcttcaagag    60
ggcagtgcct tcccaaccat tcccttatcc aggcttttg acaacgctat gctccgcgcc   120
catcgtctgc accagctggc ctttgacacc taccaggagt tgtaagctc ttggggaatg   180 gagtctattc cgacaccctc aacagggag gaaacacaac agaaatcc                228

<210> SEQ ID NO 6
<211> LENGTH: 76
<212> TYPE: PRT
<213> ORGANISM: Homo sapiens

<400> SEQUENCE: 6

Gly Ser Arg Thr Ser Leu Leu Leu Ala Phe Gly Leu Leu Cys Leu Pro
1               5                   10                  15

Trp Leu Gln Glu Gly Ser Ala Phe Pro Thr Ile Pro Leu Ser Arg Leu
                20                  25                  30

Phe Asp Asn Ala Met Leu Arg Ala His Arg Leu His Gln Leu Ala Phe
            35                  40                  45

Asp Thr Tyr Gln Glu Phe Val Ser Ser Trp Gly Met Glu Ser Ile Pro
        50                  55                  60

Thr Pro Ser Asn Arg Glu Glu Thr Gln Gln Lys Ser
65                  70                  75

<210> SEQ ID NO 7
<211> LENGTH: 600
<212> TYPE: DNA
<213> ORGANISM: Homo sapiens

<400> SEQUENCE: 7

```
atggctacag gctcccggac gtccctgctc ctggcttttg gcctgctctg cctgccctgg      60
cttcaagagg gcagtgcctt cccaaccatt cccttatcca ggcttttga caacgctatg     120
ctccgcgccc atcgtctgca ccagctggcc tttgacacct accaggagtt tgtaagctct     180
tggggaatgg agtctattcc gacaccctcc aacaggagg aaacacaaca gaaatccaac      240
ctagagctgc tccgcatctc cctgctgctc atccagtcgt ggctggagcc cgtgcagttc     300
ctcaggagtg tcttcgccaa cagcctggtg tacggcgcct ctgacagcaa cgtctatgac     360
ctcctaaagg acctagagga aggcatccaa acgctgatgg ggaggctgga agatggcagc     420
ccccggactg gcagatcttc aagcagacc tacagcaagt tcgacacaaa ctcacacaac      480
gatgacgcac tactcaagaa ctacgggctg ctctactgct tcaggaagga catggacaag     540
gtcgagacat tcctgcgcat cgtgcagtgc cgctctgtgg agggcagctg tggcttctag     600
```

<210> SEQ ID NO 8
<211> LENGTH: 199
<212> TYPE: PRT
<213> ORGANISM: Homo sapiens

<400> SEQUENCE: 8

```
Met Ala Thr Gly Ser Arg Thr Ser Leu Leu Ala Phe Gly Leu Leu
1               5                  10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Val Ser Ser Trp Gly Met Glu
    50                  55                  60

Ser Ile Pro Thr Pro Ser Asn Arg Glu Glu Thr Gln Gln Lys Ser Asn
65                  70                  75                  80

Leu Glu Leu Leu Arg Ile Ser Leu Leu Leu Ile Gln Ser Trp Leu Glu
                85                  90                  95

Pro Val Gln Phe Leu Arg Ser Val Phe Ala Asn Ser Leu Val Tyr Gly
            100                 105                 110

Ala Ser Asp Ser Asn Val Tyr Asp Leu Leu Lys Asp Leu Glu Glu Gly
        115                 120                 125

Ile Gln Thr Leu Met Gly Arg Leu Glu Asp Gly Ser Pro Arg Thr Gly
    130                 135                 140

Gln Ile Phe Lys Gln Thr Tyr Ser Lys Phe Asp Thr Asn Ser His Asn
145                 150                 155                 160

Asp Asp Ala Leu Leu Lys Asn Tyr Gly Leu Leu Tyr Cys Phe Arg Lys
                165                 170                 175

Asp Met Asp Lys Val Glu Thr Phe Leu Arg Ile Val Gln Cys Arg Ser
            180                 185                 190

Val Glu Gly Ser Cys Gly Phe
        195
```

<210> SEQ ID NO 9
<211> LENGTH: 522
<212> TYPE: DNA
<213> ORGANISM: Homo sapiens

<400> SEQUENCE: 9

```
ttcccaacca ttcccttatc caggcttttt gacaacgcta tgctccgcgc ccatcgtctg      60
```

```
caccagctgg cctttgacac ctaccaggag tttgtaagct cttggggaat ggagtctatt      120
ccgacaccct ccaacaggga ggaaacacaa cagaaatcca acctagagct gctccgcatc      180
tccctgctgc tcatccagtc gtggctggag cccgtgcagt tcctcaggag tgtcttcgcc      240
aacagcctgg tgtacggcgc tctgacagca acgtctatg acctcctaaa ggacctagag       300
gaaggcatcc aaacgctgat ggggaggctg aagatggca gccccggac tgggcagatc        360 ttcaagcaga cctacagcaa gttcgacaca aactcacaca acgatgacgc actactcaag      420
aactacgggc tgctctactg cttcaggaag gacatggaca aggtcgagac attcctgcgc      480
atcgtgcagt gccgctctgt ggagggcagc tgtggcttct ag                        522
```

```
<210> SEQ ID NO 10
<211> LENGTH: 173
<212> TYPE: PRT
<213> ORGANISM: Homo sapiens

<400> SEQUENCE: 10

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Val
            20                  25                  30

Ser Ser Trp Gly Met Glu Ser Ile Pro Thr Pro Ser Asn Arg Glu Glu
        35                  40                  45

Thr Gln Gln Lys Ser Asn Leu Glu Leu Leu Arg Ile Ser Leu Leu Leu
    50                  55                  60

Ile Gln Ser Trp Leu Glu Pro Val Gln Phe Leu Arg Ser Val Phe Ala
65                  70                  75                  80

Asn Ser Leu Val Tyr Gly Ala Ser Asp Ser Asn Val Tyr Asp Leu Leu
                85                  90                  95

Lys Asp Leu Glu Glu Gly Ile Gln Thr Leu Met Gly Arg Leu Glu Asp
            100                 105                 110

Gly Ser Pro Arg Thr Gly Gln Ile Phe Lys Gln Thr Tyr Ser Lys Phe
        115                 120                 125

Asp Thr Asn Ser His Asn Asp Asp Ala Leu Leu Lys Asn Tyr Gly Leu
    130                 135                 140

Leu Tyr Cys Phe Arg Lys Asp Met Asp Lys Val Glu Thr Phe Leu Arg
145                 150                 155                 160

Ile Val Gln Cys Arg Ser Val Glu Gly Ser Cys Gly Phe
                165                 170
```

```
<210> SEQ ID NO 11
<211> LENGTH: 37
<212> TYPE: DNA
<213> ORGANISM: Artificial Sequence
<220> FEATURE:
<223> OTHER INFORMATION: Primer GCP Forward

<400> SEQUENCE: 11
ggggacaagt ttgtacaaaa aagcaggctt cgccacc                               37
```

```
<210> SEQ ID NO 12
<211> LENGTH: 51
<212> TYPE: DNA
<213> ORGANISM: Artificial Sequence
<220> FEATURE:
<223> OTHER INFORMATION: Primer GCP Reverse

<400> SEQUENCE: 12
```
ggggaccact tgtacaaga aagctgggtt tcaatggtga tggtgatggt g        51

<210> SEQ ID NO 13
<211> LENGTH: 40
<212> TYPE: DNA
<213> ORGANISM: Artificial Sequence
<220> FEATURE:
<223> OTHER INFORMATION: Primer INSP101-B1P-5'-F

<400> SEQUENCE: 13
gcaggcttcg ccaccatggc tacaggctcc cggacgtccc                    40

<210> SEQ ID NO 14
<211> LENGTH: 50
<212> TYPE: DNA
<213> ORGANISM: Artificial Sequence
<220> FEATURE:
<223> OTHER INFORMATION: Primer INSP101-5'-R

<400> SEQUENCE: 14
tagactccat tccccaagag cttacaaact cctggtaggt gtcaaaggcc         50

<210> SEQ ID NO 15
<211> LENGTH: 51
<212> TYPE: DNA
<213> ORGANISM: Artificial Sequence
<220> FEATURE:
<223> OTHER INFORMATION: Primer INSP101-3'-F

<400> SEQUENCE: 15
aggagtttgt aagctcttgg ggaatggagt ctattccgac accctccaac a       51

<210> SEQ ID NO 16
<211> LENGTH: 39
<212> TYPE: DNA
<213> ORGANISM: Artificial Sequence
<220> FEATURE:
<223> OTHER INFORMATION: Primer INSP101-3'-R

<400> SEQUENCE: 16
gtgatggtga tggtgctaga agccacagct gccctccac                     39

<210> SEQ ID NO 17
<211> LENGTH: 36
<212> TYPE: DNA
<213> ORGANISM: Artificial Sequence
<220> FEATURE:
<223> OTHER INFORMATION: Primer INSP101-mut-F

<400> SEQUENCE: 17
gggcagctgt ggcttccacc atcaccatca ccattg                        36

<210> SEQ ID NO 18
<211> LENGTH: 37
<212> TYPE: DNA
<213> ORGANISM: Artificial Sequence
<220> FEATURE:
<223> OTHER INFORMATION: Primer INSP101-mut-R

<400> SEQUENCE: 18
aatggtgatg gtgatggtgg aagccacagc tgccctc                       37

<210> SEQ ID NO 19
<211> LENGTH: 20
<212> TYPE: DNA

```
<213> ORGANISM: Artificial Sequence
<220> FEATURE:
<223> OTHER INFORMATION: Primer pEAK12-F

<400> SEQUENCE: 19
gccagcttgg cacttgatgt                                              20

<210> SEQ ID NO 20
<211> LENGTH: 20
<212> TYPE: DNA
<213> ORGANISM: Artificial Sequence
<220> FEATURE:
<223> OTHER INFORMATION: Primer pEAK12-R

<400> SEQUENCE: 20
gatggaggtg gacgtgtcag                                              20

<210> SEQ ID NO 21
<211> LENGTH: 18
<212> TYPE: DNA
<213> ORGANISM: Artificial Sequence
<220> FEATURE:
<223> OTHER INFORMATION: Primer M13F

<400> SEQUENCE: 21
caggaaacag ctatgacc                                                18

<210> SEQ ID NO 22
<211> LENGTH: 18
<212> TYPE: DNA
<213> ORGANISM: Artificial Sequence
<220> FEATURE:
<223> OTHER INFORMATION: Primer M13R

<400> SEQUENCE: 22
tgtaaaacga cggccagt                                                18

<210> SEQ ID NO 23
<211> LENGTH: 22
<212> TYPE: DNA
<213> ORGANISM: Artificial Sequence
<220> FEATURE:
<223> OTHER INFORMATION: Primer INSP101-CP1

<400> SEQUENCE: 23
gctgcaatgg ctacaggctc cc                                           22

<210> SEQ ID NO 24
<211> LENGTH: 20
<212> TYPE: DNA
<213> ORGANISM: Artificial Sequence
<220> FEATURE:
<223> OTHER INFORMATION: Primer INSP101-CP2

<400> SEQUENCE: 24
agaagccaca gctgccctcc                                              20

<210> SEQ ID NO 25
<211> LENGTH: 677
<212> TYPE: DNA
<213> ORGANISM: Homo sapiens

<400> SEQUENCE: 25
acaagtttgt acaaaaaagc aggcttcgcc accatggcta caggctcccg gacgtccctg     60
ctcctggctt ttggcctgct ctgcctgccc tggcttcaag agggcagtgc cttcccaacc    120
```

```
attcccttat ccaggcttt  tgacaacgct atgctccgcg cccatcgtct gcaccagctg      180
gcctttgaca cctaccagga gtttgtaagc tcttggggaa tggagtctat tccgacaccc      240
tccaacaggg aggaaacaca acagaaatcc aacctagagc tgctccgcat ctccctgctg      300
ctcatccagt cgtggctgga gcccgtgcag ttcctcagga gtgtcttcgc caacagcctg      360
gtgtacggcg cctctgacag caacgtctat gacctcctaa aggacctaga ggaaggcatc      420
caaacgctga tggggaggct ggaagatggc agccccggac tgggcagat  cttcaagcag      480 acctacagca gttcgacac  aaactcacac aacgatgacg cactactcaa gaactacggg      540
ctgctctact gcttcaggaa ggacatggac aaggtcgaga cattcctgcg catcgtgcag      600
tgccgctctg tggagggcag ctgtggcttc caccatcacc atcaccattg aaacccagct      660
ttcttgtaca aagtggt                                                    677
```

<210> SEQ ID NO 26
<211> LENGTH: 205
<212> TYPE: PRT
<213> ORGANISM: Homo sapiens
<400> SEQUENCE: 26

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
             35                  40                  45

Leu Ala Phe Asp Thr Tyr Gln Glu Phe Val Ser Ser Trp Gly Met Glu
 50                  55                  60

Ser Ile Pro Thr Pro Ser Asn Arg Glu Glu Thr Gln Gln Lys Ser Asn
 65                  70                  75                  80

Leu Glu Leu Leu Arg Ile Ser Leu Leu Leu Ile Gln Ser Trp Leu Glu
                 85                  90                  95

Pro Val Gln Phe Leu Arg Ser Val Phe Ala Asn Ser Leu Val Tyr Gly
                100                 105                 110

Ala Ser Asp Ser Asn Val Tyr Asp Leu Leu Lys Asp Leu Glu Glu Gly
             115                 120                 125

Ile Gln Thr Leu Met Gly Arg Leu Glu Asp Gly Ser Pro Arg Thr Gly
130                 135                 140

Gln Ile Phe Lys Gln Thr Tyr Ser Lys Phe Asp Thr Asn Ser His Asn
145                 150                 155                 160

Asp Asp Ala Leu Leu Lys Asn Tyr Gly Leu Leu Tyr Cys Phe Arg Lys
                165                 170                 175

Asp Met Asp Lys Val Glu Thr Phe Leu Arg Ile Val Gln Cys Arg Ser
                180                 185                 190

Val Glu Gly Ser Cys Gly Phe His His His His His
            195                 200                 205
```